US010857302B2

(12) United States Patent
Shang et al.

(10) Patent No.: US 10,857,302 B2
(45) Date of Patent: Dec. 8, 2020

(54) AUTOMATIC INJECTION DEVICE

(71) Applicant: AbbVie Inc., North Chicago, IL (US)

(72) Inventors: Sherwin S. Shang, Vernon Hills, IL (US); Joseph F. Julian, Libertyville, IL (US); Chuan Li, Deerfield, IL (US); Eduard N. Tsvirko, Arlington Heights, IL (US); Edwin Chim, Vernon Hills, IL (US); Shubha Chethan Somashekar, Waukegan, IL (US); Esra Ozdaryal, Deerfield, IL (US)

(73) Assignee: AbbVie Inc., North Chicago, IL (US)

( * ) Notice: Subject to any disclaimer, the term of this patent is extended or adjusted under 35 U.S.C. 154(b) by 196 days.

(21) Appl. No.: 15/990,065

(22) Filed: May 25, 2018

(65) Prior Publication Data

US 2018/0272069 A1 Sep. 27, 2018

Related U.S. Application Data

(63) Continuation of application No. 14/673,463, filed on Mar. 30, 2015, now Pat. No. 9,981,087, which is a
(Continued)

(51) Int. Cl.
*A61M 5/315* (2006.01)
*A61M 5/20* (2006.01)
*A61M 5/31* (2006.01)

(52) U.S. Cl.
CPC .......... *A61M 5/31501* (2013.01); *A61M 5/20* (2013.01); *A61M 5/2033* (2013.01);
(Continued)

(58) Field of Classification Search
CPC .. A61M 2005/2006; A61M 2005/3126; A61M 2205/583; A61M 2205/584;
(Continued)

(56) References Cited

U.S. PATENT DOCUMENTS 3,702,609 A 11/1972 Steiner
3,910,260 A 10/1975 Sarnoff et al.
(Continued)

FOREIGN PATENT DOCUMENTS

CN 1774274 A 5/2006
CN 101479001 A 7/2009
(Continued)

OTHER PUBLICATIONS

Abbott, Abbott Receives FDA Approval for New Humira® Delivery Device, HUMIRA Pen Offers Patients Easier, Less Painful Way to Self-Administer Medicine. Press Release, dated Jun. 26, 2006. 6 pages.
(Continued)

*Primary Examiner* — Brandy S Lee
(74) *Attorney, Agent, or Firm* — McCarter & English, LLP; David R. Burns

(57) ABSTRACT

A syringe carrier for use within an automatic injection device includes a substantially tubular body having a first end, a middle portion, and a second end, configured to contain a portion of a syringe and displace the syringe within a housing of the automatic injection device from a first position to a second position; a first pair of legs defining at least a portion of a front opening in the substantially tubular body proximal to the first end; a second pair of legs defining at least a portion of a rear opening in the substantially tubular body proximal to the first end; and a syringe carrier coupler having a first beam and a second beam extending from the middle portion partially beyond the first pair of legs at the first end of the substantially tubular body.

20 Claims, 21 Drawing Sheets

Related U.S. Application Data continuation of application No. 13/624,838, filed on Sep. 21, 2012, now Pat. No. 8,992,476.

(60) Provisional application No. 61/538,098, filed on Sep. 22, 2011.

(52) U.S. Cl.
CPC ............... *A61M 2005/2006* (2013.01); *A61M 2005/3126* (2013.01); *A61M 2205/583* (2013.01); *A61M 2205/584* (2013.01); *A61M 2205/60* (2013.01); *F04C 2270/041* (2013.01)

(58) Field of Classification Search
CPC .. A61M 2205/60; A61M 5/20; A61M 5/2033; A61M 5/31501
See application file for complete search history.

(56) References Cited

U.S. PATENT DOCUMENTS

| | | | |
|---|---|---|---|
| 3,941,130 | A | 3/1976 | Tibbs |
| 4,004,577 | A | 1/1977 | Sarnoff |
| 4,261,358 | A | 4/1981 | Vargas et al. |
| 4,637,403 | A | 1/1987 | Garcia et al. |
| 4,689,042 | A | 8/1987 | Sarnoff et al. |
| 4,755,169 | A | 7/1988 | Sarnoff et al. |
| 4,795,433 | A | 1/1989 | Sarnoff |
| 4,936,833 | A | 6/1990 | Sams |
| 5,085,642 | A | 2/1992 | Sarnoff et al. |
| 5,092,843 | A | 3/1992 | Monroe et al. |
| 5,102,393 | A | 4/1992 | Sarnoff et al. |
| 5,267,963 | A | 12/1993 | Bachynsky |
| 5,320,609 | A | 6/1994 | Haber et al. |
| 5,378,233 | A | 1/1995 | Haber et al. |
| 5,645,534 | A | 7/1997 | Chanoch |
| 5,674,204 | A | 10/1997 | Chanoch |
| 5,744,360 | A | 4/1998 | Hu et al. |
| 5,921,966 | A | 7/1999 | Bendek et al. |
| 5,993,421 | A | 11/1999 | Kriesel |
| 6,149,626 | A | 11/2000 | Bachynsky et al. |
| 6,221,044 | B1 | 4/2001 | Greco |
| 6,270,479 | B1 | 8/2001 | Bergens et al. |
| 6,277,099 | B1 | 8/2001 | Strowe et al. |
| 6,371,939 | B2 | 4/2002 | Bergens et al. |
| 6,805,686 | B1 | 10/2004 | Fathallah et al. |
| 7,229,432 | B2 | 6/2007 | Marshall et al. |
| 7,235,056 | B2 | 6/2007 | Duchon et al. |
| 7,938,802 | B2 | 5/2011 | Bicknell et al. |
| 8,162,887 | B2 | 4/2012 | Bicknell et al. |
| 8,298,194 | B2 | 10/2012 | Moller |
| 8,608,709 | B2 | 12/2013 | Moller et al. |
| 8,636,704 | B2 | 1/2014 | Shang et al. |
| 8,679,061 | B2 | 3/2014 | Julian et al. |
| 8,758,301 | B2 | 6/2014 | Shang et al. |
| 8,915,889 | B2 | 12/2014 | Cox et al. |
| 8,992,476 | B2 | 3/2015 | Shang et al. |
| 9,072,833 | B2 | 7/2015 | Jennings et al. |
| 9,119,920 | B2 | 9/2015 | Cowe |
| 9,192,727 | B2 | 11/2015 | Moller et al. |
| 9,220,660 | B2 | 12/2015 | Sund et al. |
| 9,265,887 | B2 | 2/2016 | Julian et al. |
| 9,408,973 | B2 | 8/2016 | Shang et al. |
| 9,443,445 | B2 | 9/2016 | Laurusonis et al. |
| 9,592,347 | B2 | 3/2017 | Nzike et al. |
| 9,597,460 | B2 | 3/2017 | Saiki |
| 9,943,649 | B2 | 4/2018 | Shang et al. |
| 9,981,087 | B2 | 5/2018 | Shang et al. |
| 2002/0002344 | A1 | 1/2002 | Douglas et al. |
| 2002/0169408 | A1 | 11/2002 | Beretta et al. |
| 2003/0229308 | A1 | 12/2003 | Tsals et al. |
| 2006/0047250 | A1 | 3/2006 | Hickingbotham et al. |
| 2006/0167413 | A1 | 7/2006 | Marshall et al. |
| 2007/0142776 | A9 | 6/2007 | Kovelman et al. |
| 2007/0161960 | A1 | 7/2007 | Chen et al. |
| 2008/0009806 | A1 | 1/2008 | Chang |
| 2008/0086092 | A1 | 4/2008 | Loe |
| 2009/0259194 | A1 | 10/2009 | Pinedjian et al. |
| 2010/0016795 | A1 | 1/2010 | McLoughlin |
| 2010/0160894 | A1* | 6/2010 | Julian ................ A61M 5/2033 604/506 |
| 2010/0305512 | A1 | 12/2010 | Guillermo et al. |
| 2011/0054414 | A1 | 3/2011 | Shang et al. |
| 2011/0178500 | A1 | 7/2011 | Shang et al. |
| 2011/0184351 | A1 | 7/2011 | Holmqvist |
| 2011/0295215 | A1 | 12/2011 | Nielsen et al. |
| 2012/0056401 | A1 | 3/2012 | Beale et al. |
| 2012/0123350 | A1 | 5/2012 | Giambattista et al. |
| 2012/0197209 | A1 | 8/2012 | Bicknell et al. |
| 2012/0289905 | A1 | 11/2012 | Julian et al. |
| 2013/0060231 | A1 | 3/2013 | Adlon et al. |
| 2013/0079718 | A1 | 3/2013 | Shang et al. |
| 2013/0079725 | A1 | 3/2013 | Shang |
| 2013/0211330 | A1 | 8/2013 | Pedersen et al. |
| 2013/0236872 | A1 | 9/2013 | Laurusonis et al. |
| 2013/0338593 | A1 | 12/2013 | Wozencroft |
| 2014/0207073 | A1 | 7/2014 | Shang et al. |
| 2015/0012026 | A1 | 1/2015 | Klein et al. |
| 2015/0080811 | A1 | 3/2015 | Wieselblad |
| 2015/0224259 | A1 | 8/2015 | Giambattista et al. |
| 2015/0314073 | A1 | 11/2015 | Shang et al. |
| 2016/0151586 | A1 | 6/2016 | Kemp |
| 2016/0175528 | A1 | 6/2016 | Marshall et al. |
| 2016/0263325 | A1 | 9/2016 | Huthmacher et al. |
| 2016/0287803 | A1 | 10/2016 | Blancke et al. |
| 2018/0228980 | A1 | 8/2018 | Shang et al. |

FOREIGN PATENT DOCUMENTS

| | | |
|---|---|---|
| CN | 101484199 A | 7/2009 |
| CN | 102170929 A | 8/2011 |
| JP | 2003-260136 A | 9/2003 |
| JP | 2007-510465 A | 4/2007 |
| JP | 2007-518507 A | 7/2007 |
| JP | 2008-073530 A | 4/2008 |
| JP | 2009-542334 A | 12/2009 |
| JP | 2014-526368 A | 10/2014 |
| JP | 2014-526369 A | 10/2014 |
| RU | 2007127537 A | 2/2009 |
| WO | 2003/013632 A2 | 2/2003 |
| WO | 2005/046765 A3 | 8/2005 |
| WO | 2005/070481 A1 | 8/2005 |
| WO | 2006/000785 A1 | 1/2006 |
| WO | 2006/076921 A1 | 7/2006 |
| WO | 2008/005315 A2 | 1/2008 |
| WO | 2008/036935 A2 | 3/2008 |
| WO | 2009/081103 A1 | 7/2009 |
| WO | 2010/037828 A1 | 4/2010 |
| WO | 2011/003817 A1 | 1/2011 |
| WO | 2011/075524 A1 | 6/2011 |
| WO | 2011/109205 A2 | 9/2011 |
| WO | 2012/056401 A1 | 5/2012 |

OTHER PUBLICATIONS

Examination Report issued in New Zealand Patent Application No. 622510, dated Nov. 21, 2014.
Examination Report issued in Singapore Patent Application No. 11201400910P, dated Feb. 19, 2016.
Extended European Search Report issued in European Patent Application No. 15178649.8, dated Oct. 28, 2015.
Final Examination Report in Singapore Patent Application No. 11201400796T, dated Jan. 8, 2016.
Final Examination Report in Singapore Patent Application No. 11201400910P, dated Feb. 19, 2016.
First Examination Report issued in Australian Patent Application No. 2012312052, dated May 24, 2016.
First Office Action issued in Chinese Patent Application No. 201280057172.1, dated Sep. 25, 2015.
International Preliminary Report on Patentability for PCT/US/2012/056744, dated Mar. 25, 2014.

(56) References Cited

OTHER PUBLICATIONS

International Preliminary Report on Patentability for PCT/US/2012/056750, dated Mar. 25, 2014.
International Preliminary Report on Patentability for PCT/US/2012/056756, dated Mar. 25, 2014.
International Search Report and Written Opinion issued in International Application No. PCT/US2012/056744, dated Dec. 6, 2012.
International Search Report and Written Opinion issued in International Application No. PCT/US2012/056750, dated Dec. 6, 2012.
International Search Report and Written Opinion issued in International Application No. PCT/US2012/056756, dated Dec. 6, 2012.
Office Action issued in Chinese Patent Application No. 201280057172.1, dated Sep. 25, 2015.
Office Action issued in Chinese Patent Application No. 201280057179.3, dated Sep. 2, 2015.
Office Action issued in Japanese Patent Application No. 2014-532045, dated Sep. 2, 2016.
Office Action issued in Taiwanese Patent Application No. 101134987, dated Jan. 26, 2016.
Office Action issued in Taiwanese Patent Application No. 101134988, dated Jan. 28, 2016.
Official Decision of Grant in Russian Patent Application No. 2014115981, dated Mar. 21, 2017.
Patent Examination Report No. In Australian Patent Application No. 2012312052, dated May 24, 2016.
Second Office Action issued in Chinese Patent Application No. 201280057172.1, dated Jun. 3, 2016.
Written Opinion issued in Singapore Application No. 11201400796T, dated Apr. 7, 2015.
Written Opinion issued in Singapore Application No. 11201400908Q, dated Oct. 13, 2015.
Written Opinion issued in Singapore Application No. 11201400910P, dated Aug. 14, 2015.
US29/550,433 892 dated Sep. 21, 2017. 3 pages.
European Search Report for Application No. 18183895.4, dated Oct. 30, 2018, 11 pages.
U.S. Appl. No. 13/624,818, filed Sep. 21, 2012, U.S. Pat. No. 9,408,973, Issued.
U.S. Appl. No. 13/624,838, filed Sep. 21, 2012, U.S. Pat. No. 8,992,476, Issued.
U.S. Appl. No. 14/673,463, filed Mar. 30, 2015, U.S. Pat. No. 9,981,087, Issued.
U.S. Appl. No. 29/559,525, filed Mar. 29, 2016, U.S. Pat. No. D818,587, Issued.
U.S. Appl. No. 14/220,782, filed Mar. 20, 2014, U.S. Pat. No. 9,943,649, Issued.
U.S. Appl. No. 29/550,433, filed Jan. 4, 2016, U.S. Pat. No. D832,424, Issued.
U.S. Appl. No. 15/953,049, filed Apr. 13, 2018, U.S. Pat. No. 2018-0228980, Published.
U.S Appl. No. 29/265,691, filed Sep. 6, 2006, U.S. Pat. No. D622,374, Issued.
U.S. Appl. No. 29/265,646, filed Sep. 6, 2006, U.S. Pat. No. D629,509, Issued.
U.S. Appl. No. 11/824,516, filed Jun. 29, 2007, Abandoned.
U.S. Appl. No. 12/074,704, filed Mar. 5, 2008, U.S. Pat. No. 8,679,061, Issued.
U.S. Appl. No. 12/305,513, filed Dec. 23, 2011, Abandoned.
U.S. Appl. No. 13/267,467, filed Oct. 6, 2011, U.S. Pat. No. 9,572,938, Issued.
U.S. Appl. No. 14/170,045, filed Jan. 31, 2014, U.S. Pat. No. 2015-0037772, Abandoned.
U.S. Appl. No. 14/935,085, filed Nov. 6, 2015, U.S. Pat. No. 9,486,584, Issued.
U.S. Appl. No. 15/434,844, filed Feb. 16, 2017, U.S. Pat. No. 2017-0203041, Abandoned.

* cited by examiner

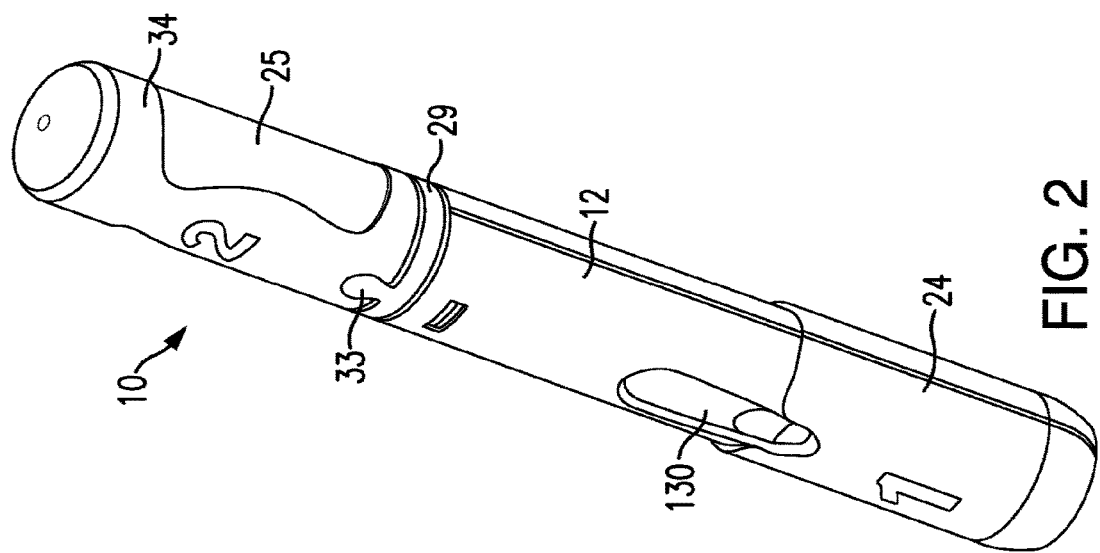
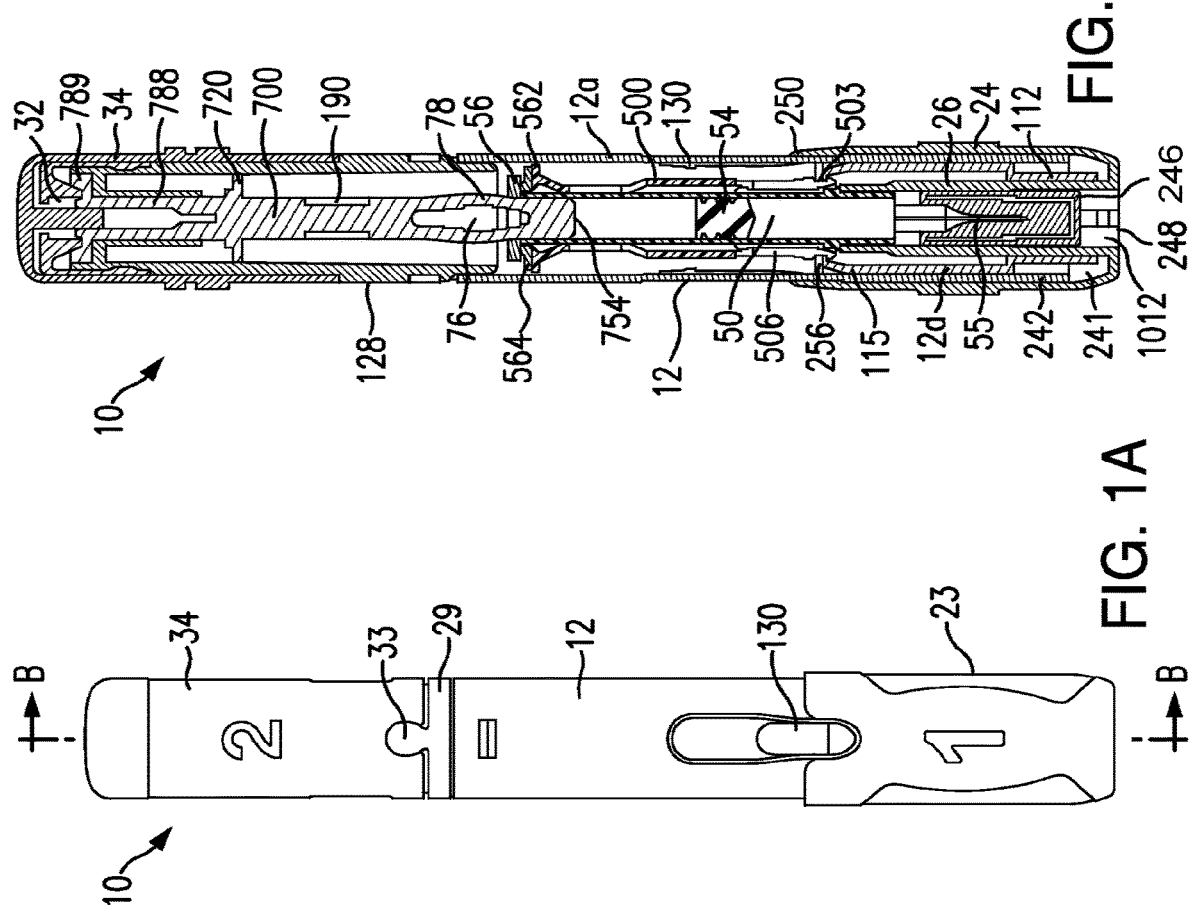

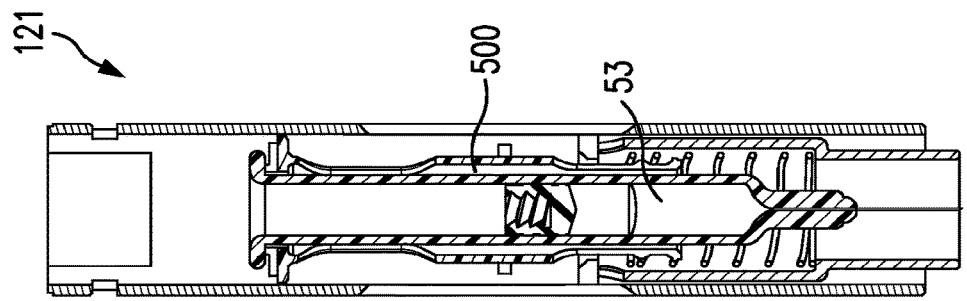
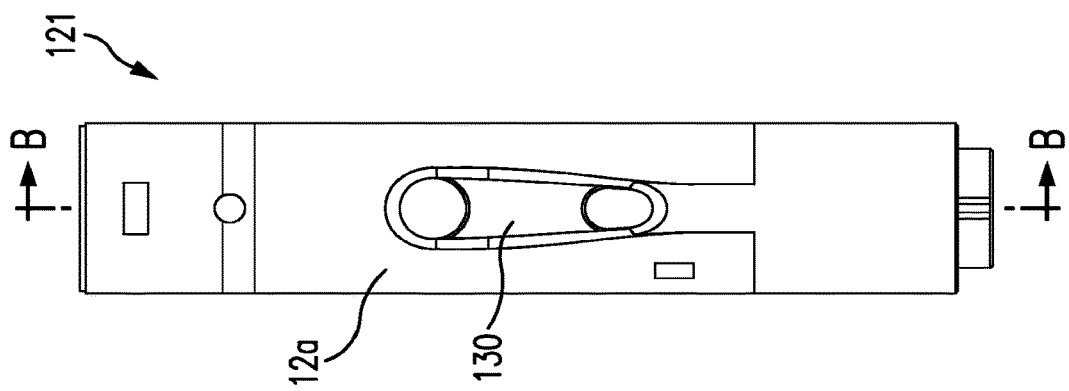
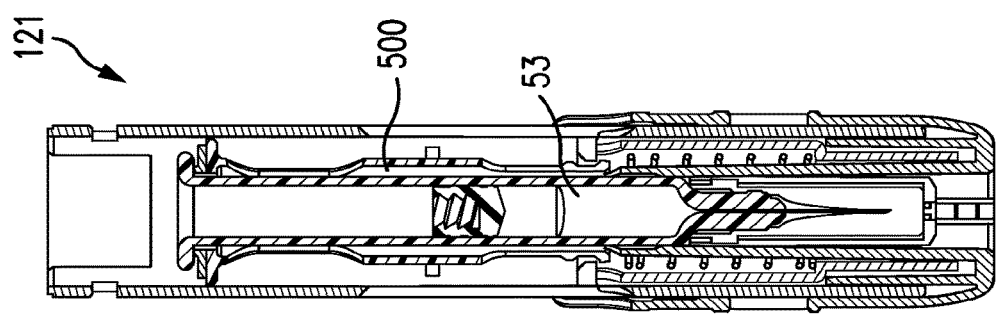
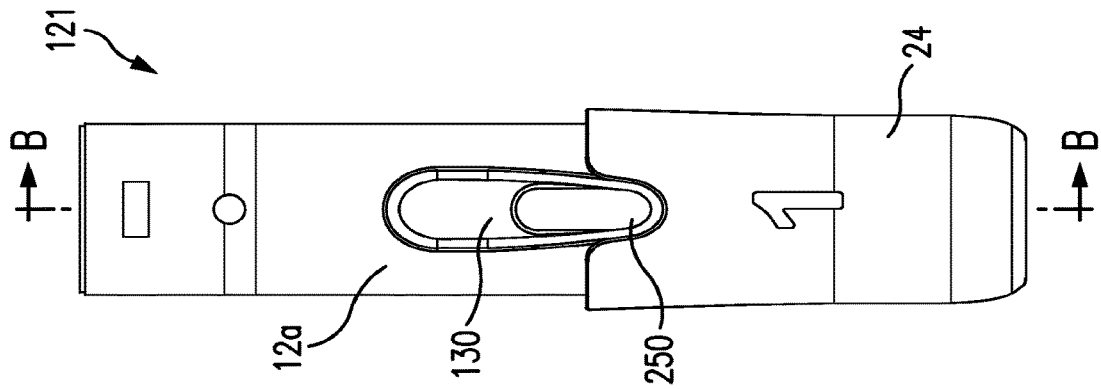
FIG. 3A
FIG. 3B
FIG. 4A
FIG. 4B

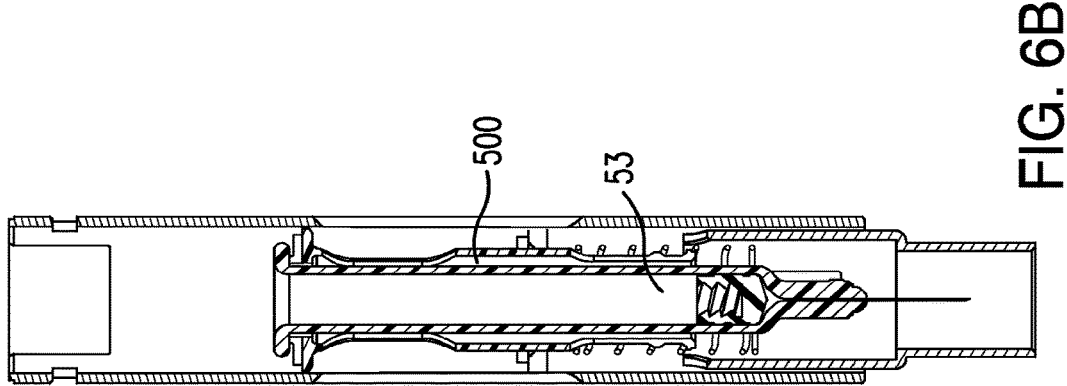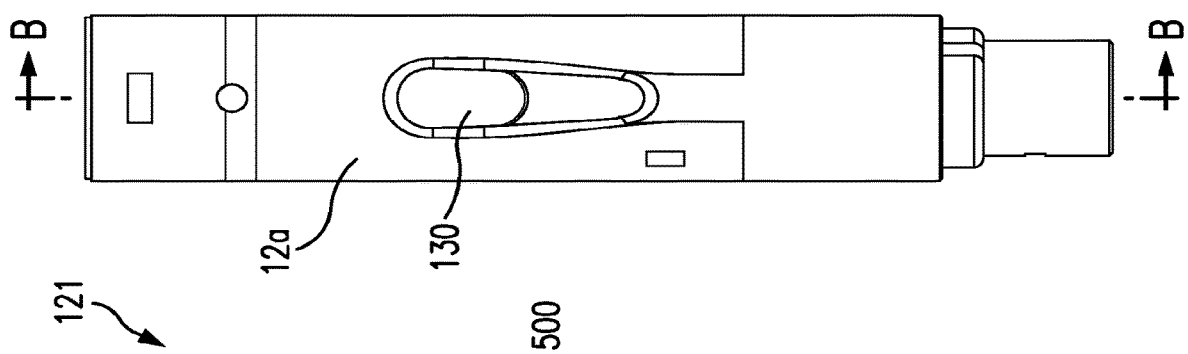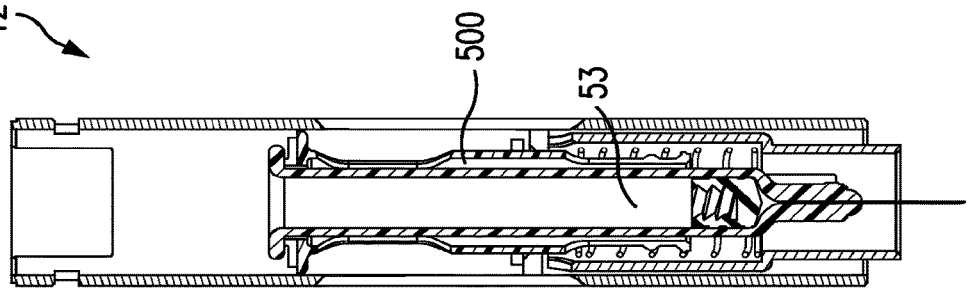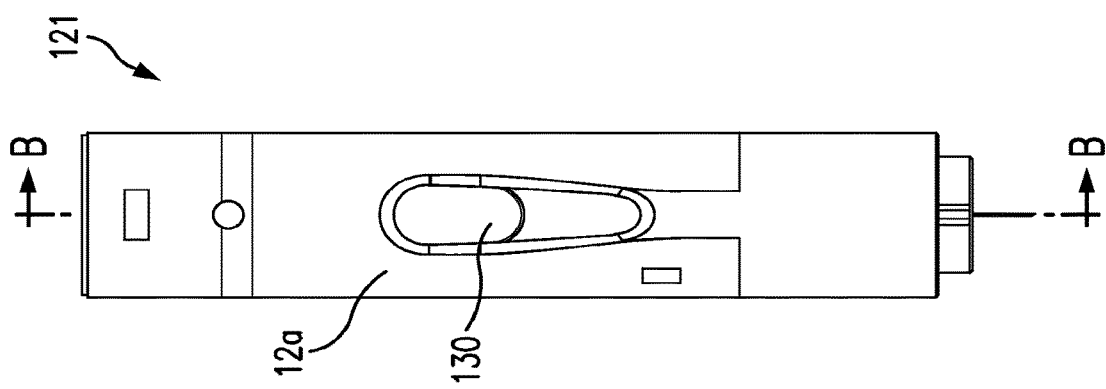

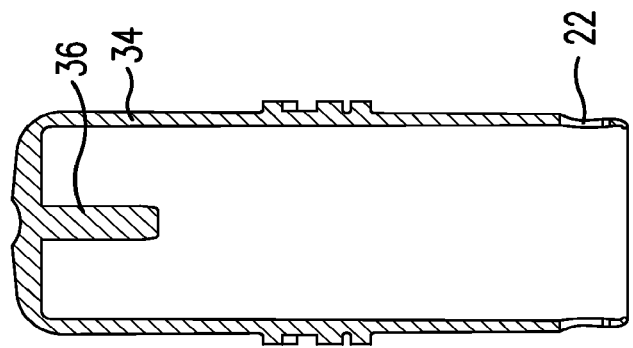
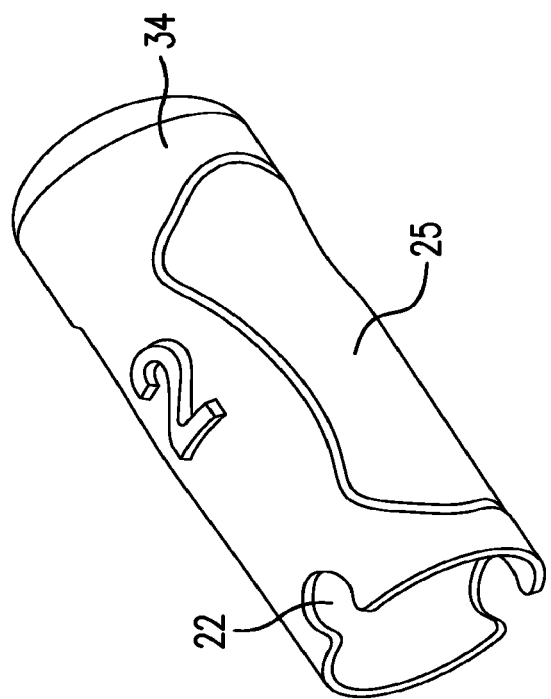
FIG. 10B
FIG. 10A

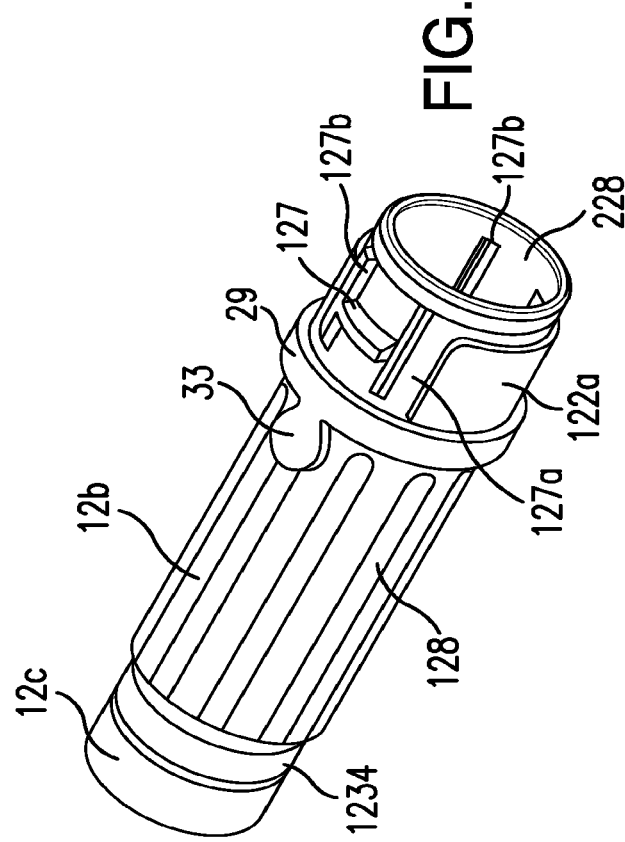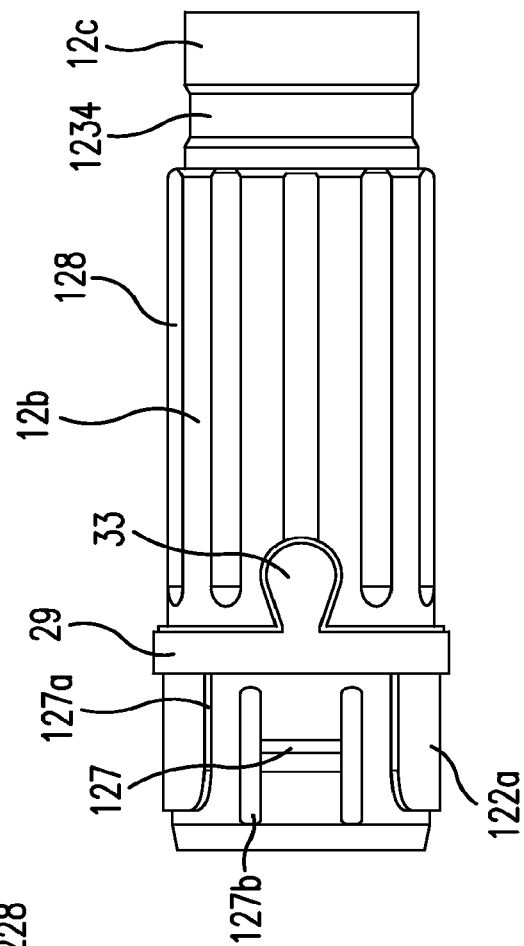

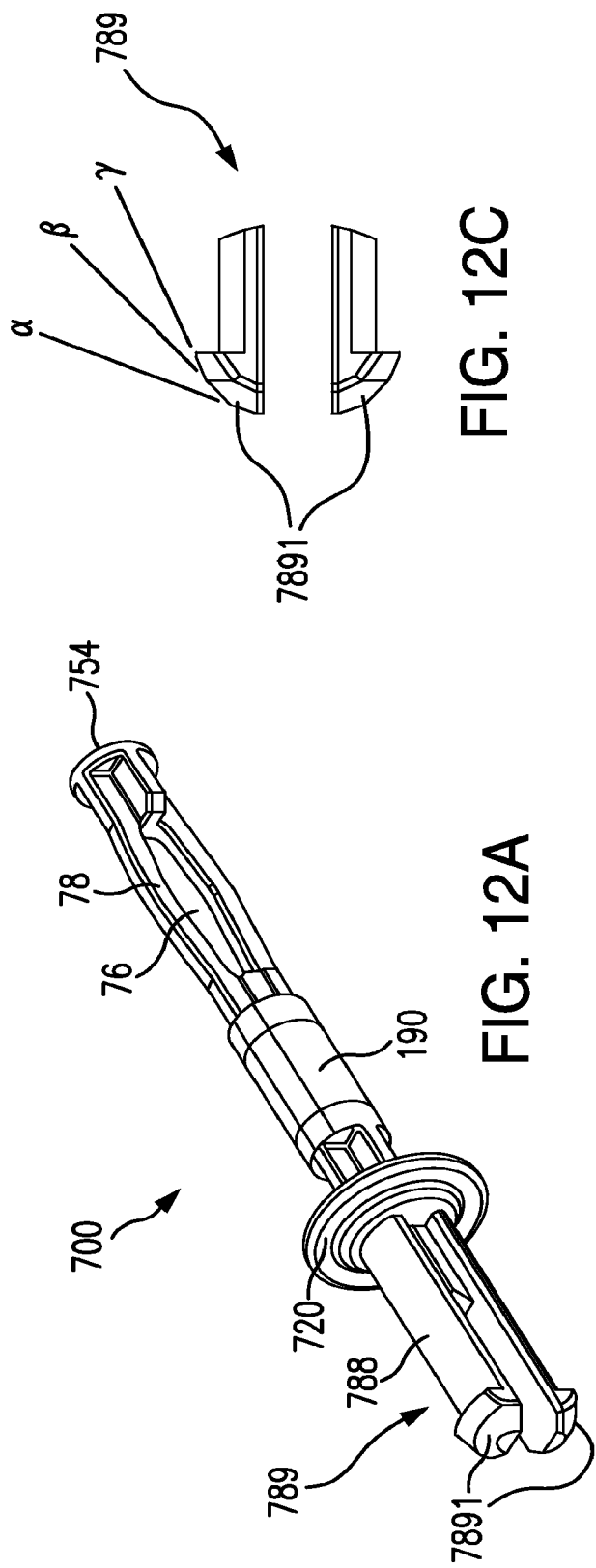
FIG. 12A
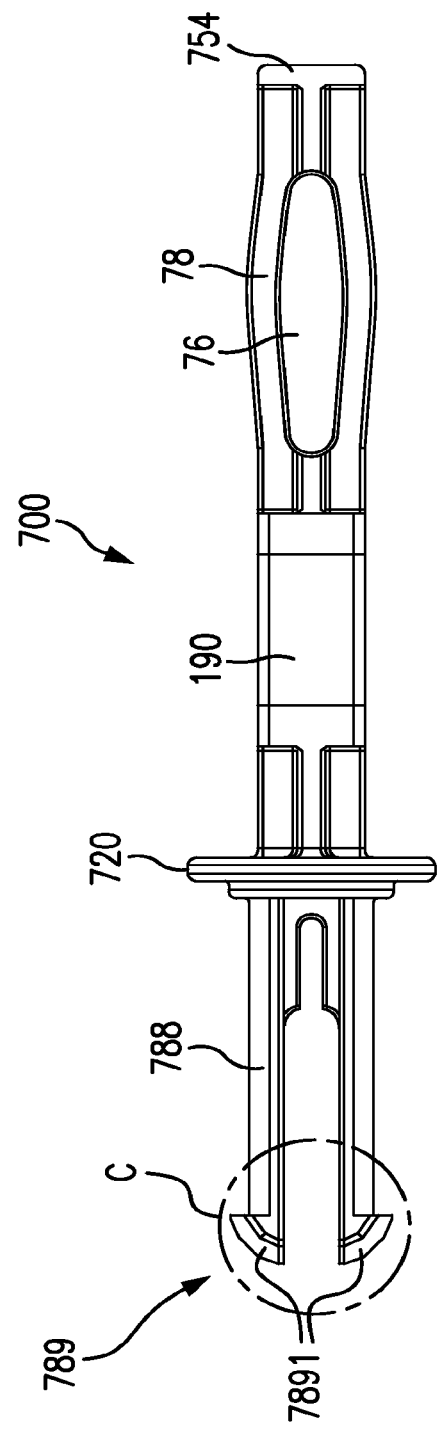
FIG. 12C
FIG. 12B

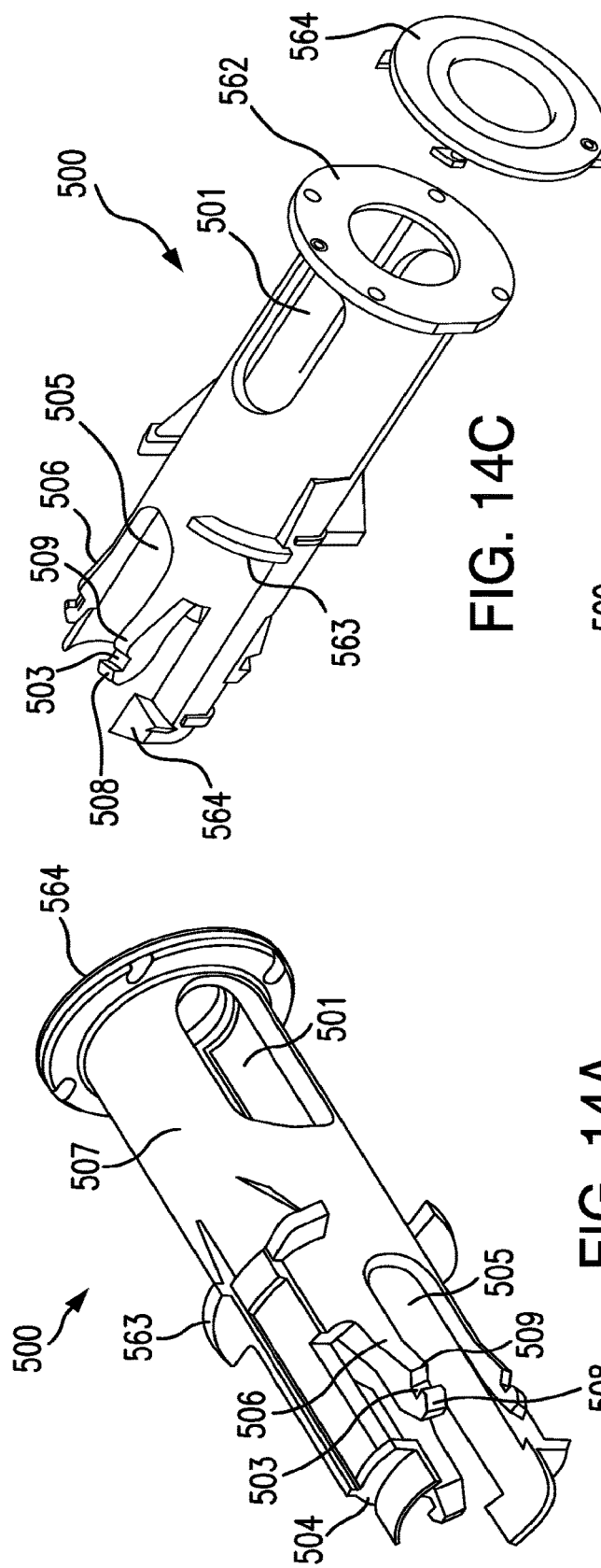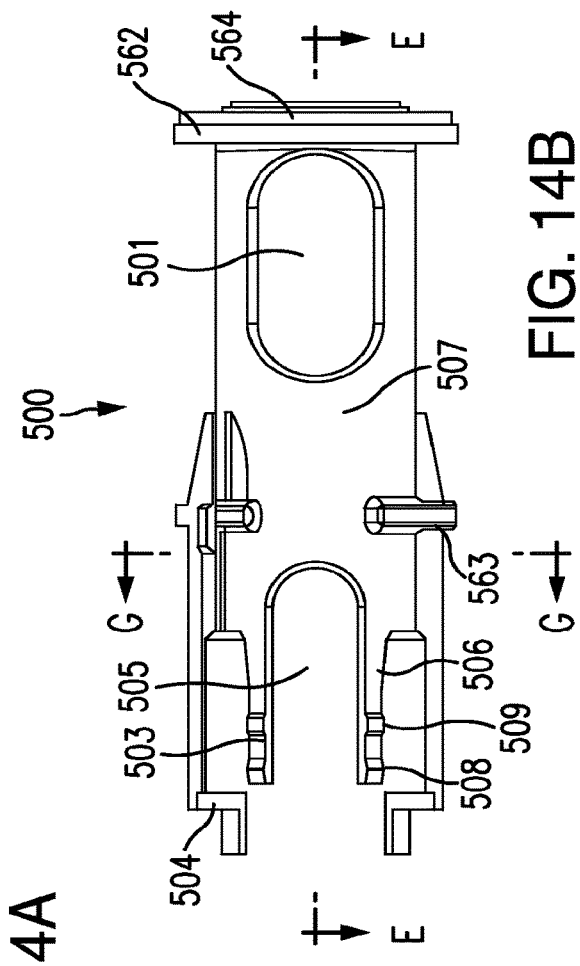

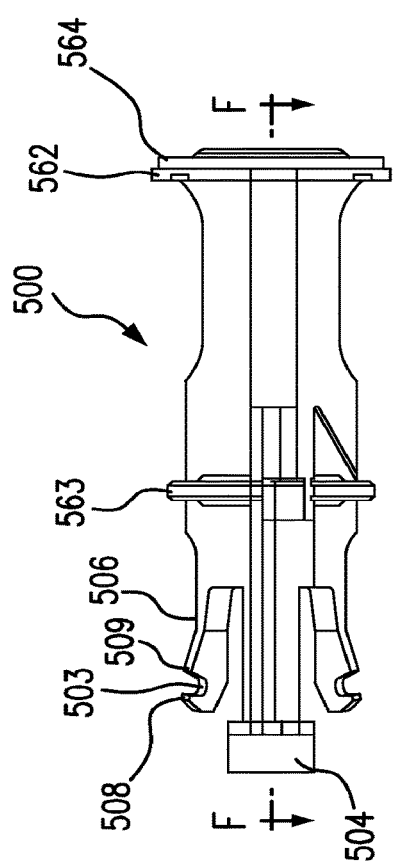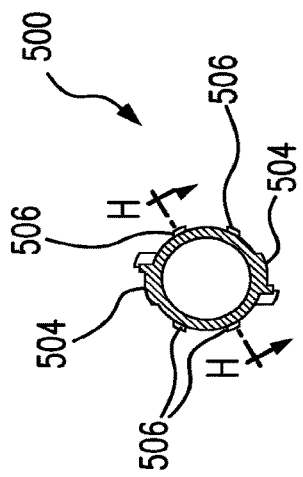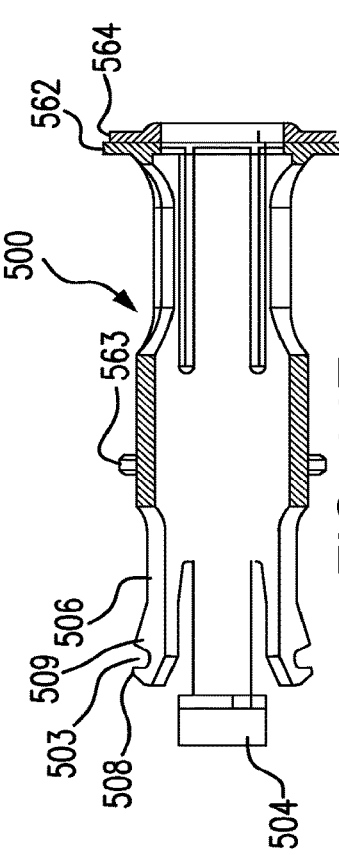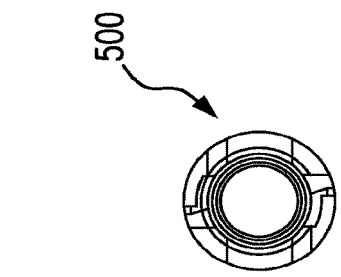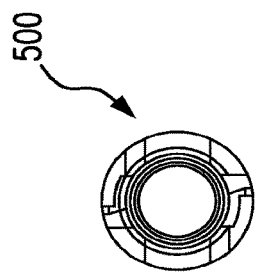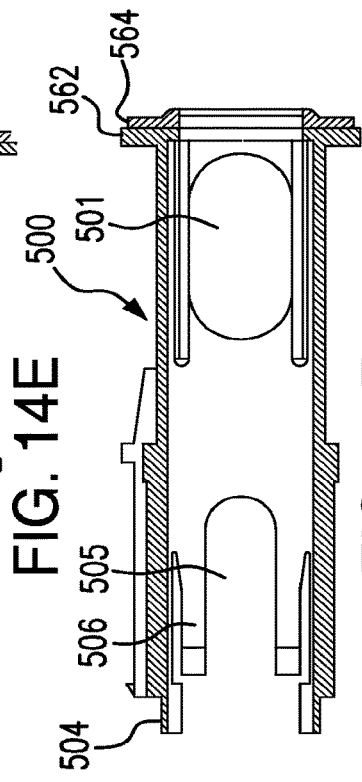

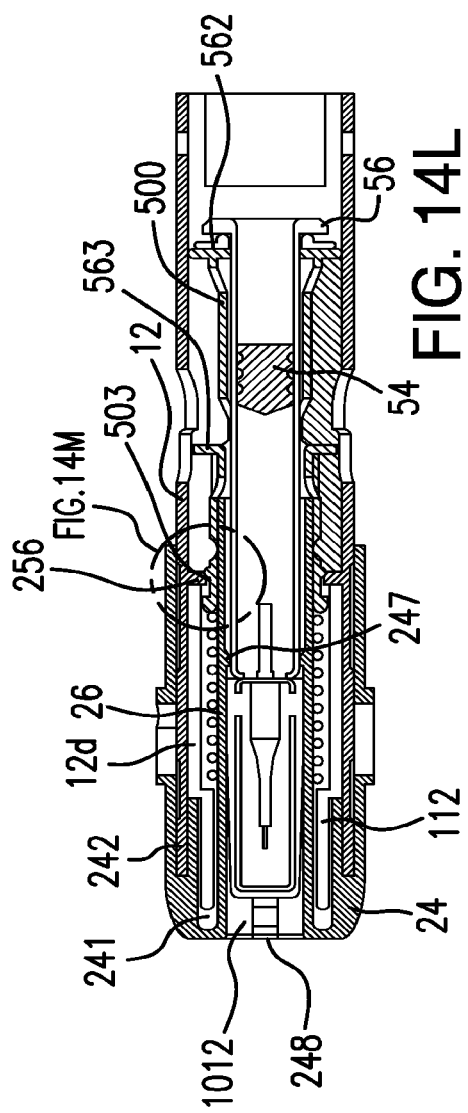
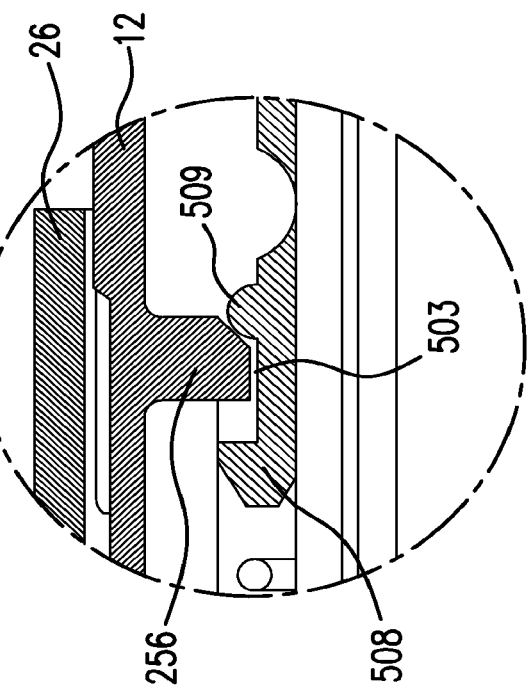

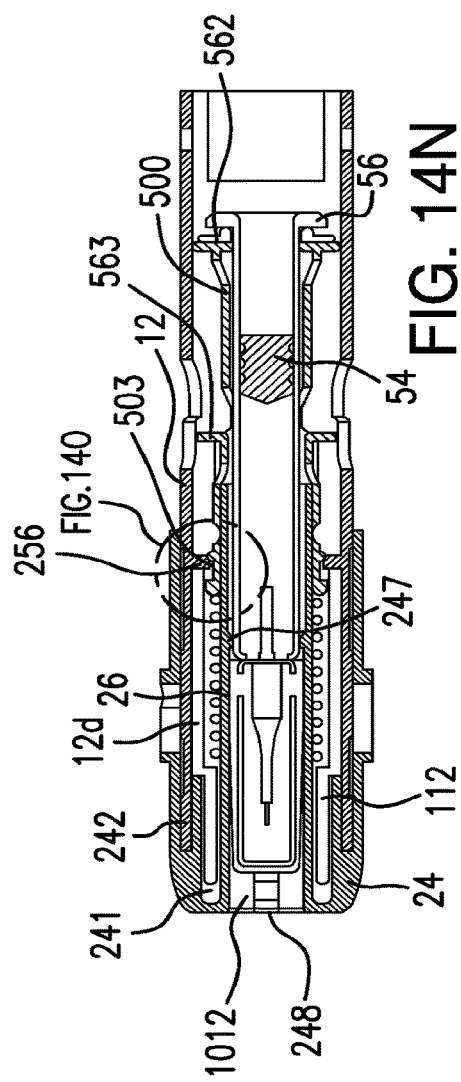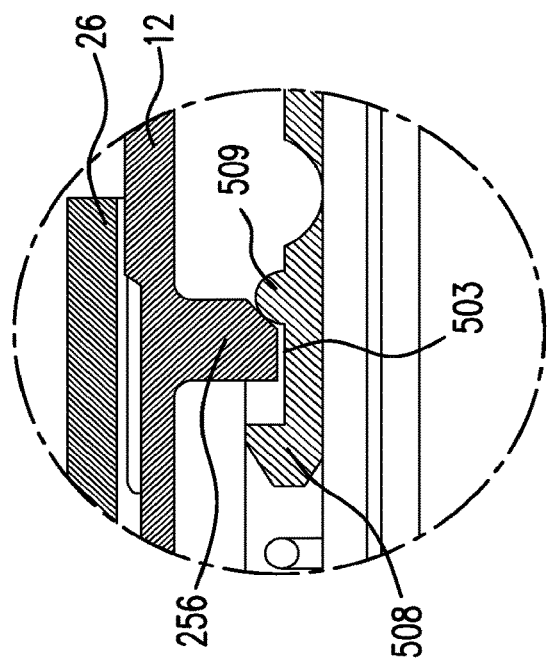

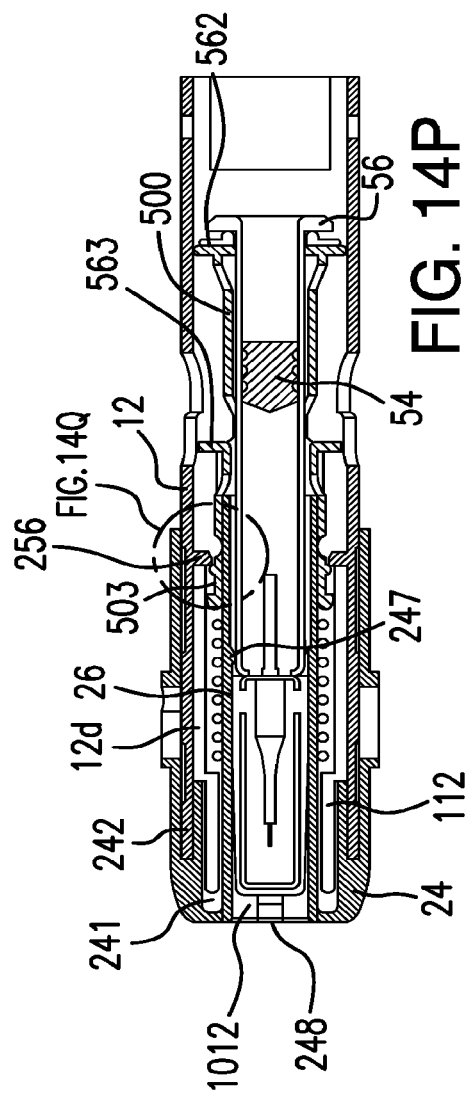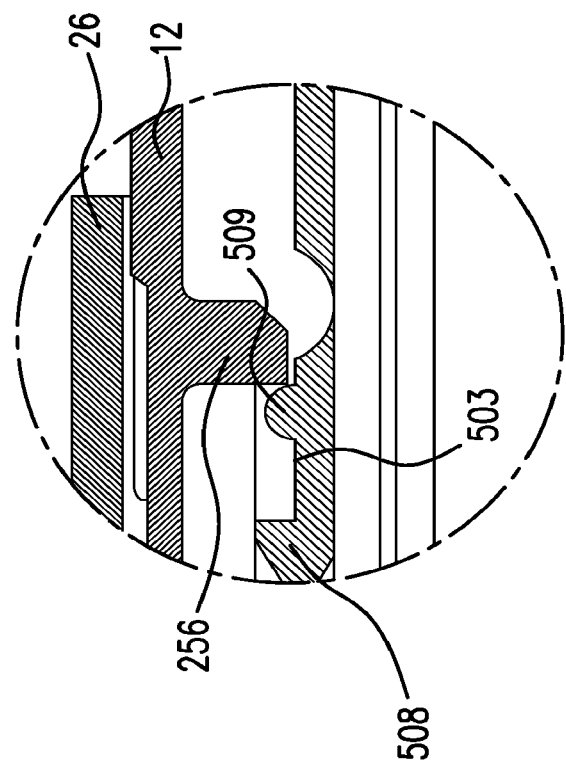

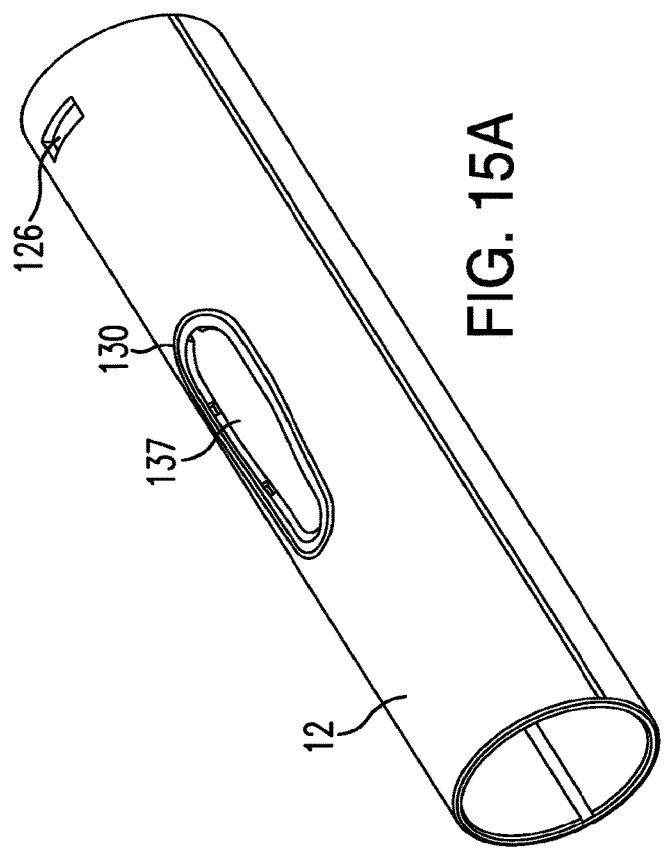
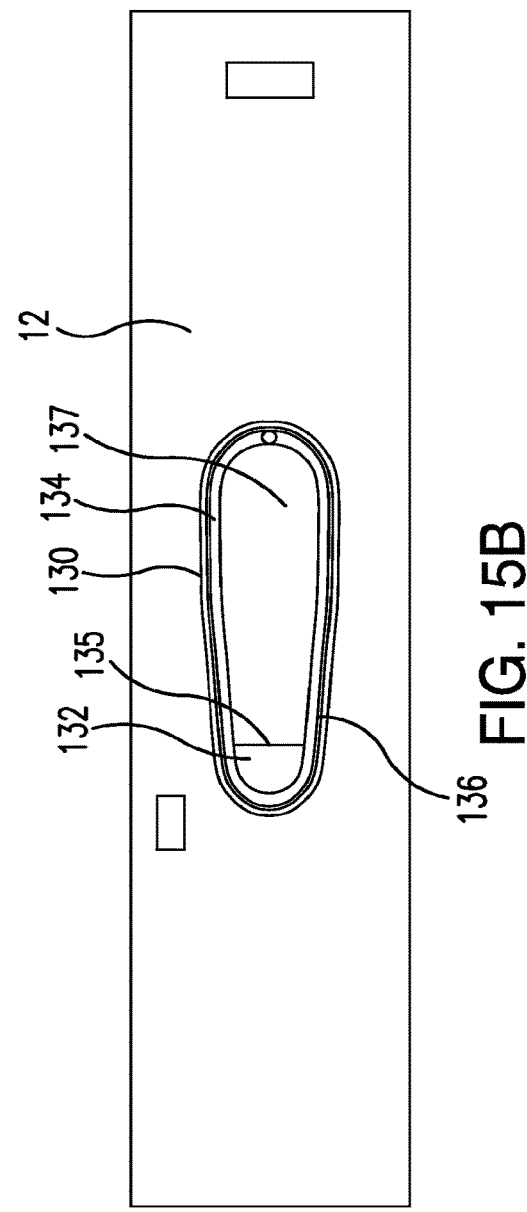

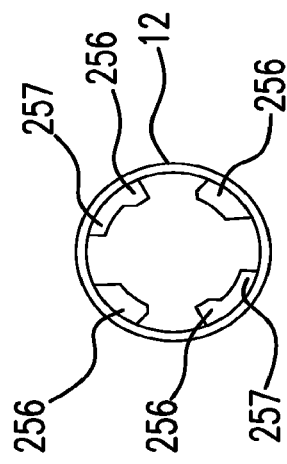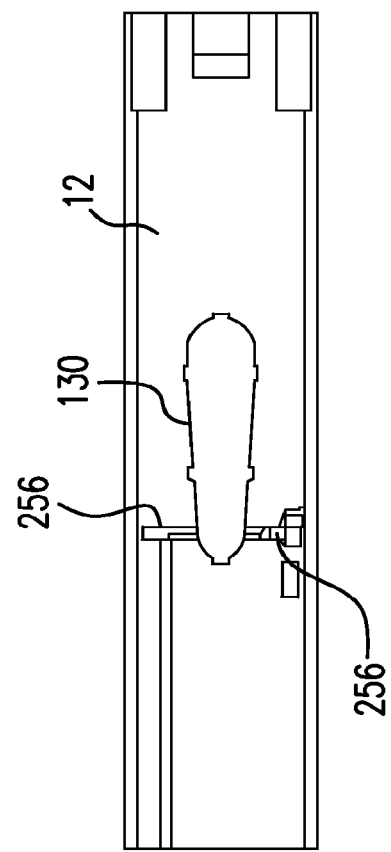

AUTOMATIC INJECTION DEVICE

CROSS-REFERENCE TO RELATED APPLICATIONS

This application is a continuation of U.S. application Ser. No. 14/673,463 filed on Mar. 30, 2015, which is a continuation of U.S. application Ser. No. 13/624,838, now U.S. Pat. No. 8,992,476, filed on Sep. 21, 2012, and which claims the benefit of priority to U.S. Provisional Application No. 61/538,098, filed on Sep. 22, 2011, all of which are incorporated by reference herein in their entirety.

This application is also related to U.S. application Ser. No. 13/624,818, now U.S. Pat. No. 9,408,973, filed on Sep. 21, 2012; U.S. application Ser. No. 14/220,782, now U.S. Pat. No. 9,943,649, filed on Mar. 20, 2014; U.S. Design application Ser. No. 29/550,433 filed on Jan. 4, 2016; U.S. Design application Ser. No. 29/559,525, now U.S. Design Pat. No. D818,587, filed on Mar. 29, 2016; and U.S. application Ser. No. 15/953,049 filed on Apr. 13, 2018, each of which is also incorporated by reference herein in their entirety.

BACKGROUND

1. Field of the Disclosed Subject Matter

The present disclosed subject matter relates to an automatic injection device for injecting a substance, such as a therapeutic agent, into a patient.

2. Description of Related Art

One of the most common routes of administration for therapeutic agents, such as medications, is by injection, such as intravenous, subcutaneous or intramuscular injection. A syringe containing the medication is used for the injection, which typically is carried out by trained medical personnel. In certain instances, a patient is trained in the use of the syringe to allow for self-injection. Moreover, certain medications are formulated in pre-filled syringes for patient use, to avoid the need for the patient to fill the syringe. Some patients, however, can be averse to carrying out self-injection, particularly if the patient has a fear of needles or limited dexterity.

Automatic injection devices offer an alternative to a syringe for delivering a therapeutic agent. Automatic injection devices have been used, for example, to deliver medications under emergency conditions, such as to administer epinephrine to counteract the effects of a severe allergic reaction, for example, as caused by a food allergy. Automatic injection devices also have been described for use in administering antiarrhythmic medications and selective thrombolytic agents during a heart attack (see e.g., U.S. Pat. Nos. 3,910,260; 4,004,577; 4,689,042; 4,755,169 and 4,795,433). Various types of automatic injection devices also are described in, for example, U.S. Pat. Nos. 3,941,130; 4,261,358; 5,085,642; 5,092,843; 5,102,393; 5,267,963; 6,149,626; 6,270,479; and 6,371,939, each of which is incorporated by reference herein in its entirety.

In general, prior automatic injection devices, when operated, have a needle of a syringe configured to move forward and project from a protective housing prior to actuation of the piston of the syringe to eject a dose of liquid through the needle. Movement of the syringe toward the patient's skin such that the needle is exposed before pressurizing a liquid charge inside the syringe can help prevent the liquid from being discharged from the needle before the actual injection takes place.

However, there remains a need for further improvement of known automatic injection devices. For example, it can be desirable to inspect the contents of the automatic injection device prior to use. Also, it can be desirable to indicate when injection is completed. Such features are available in certain automatic injection devices, the features depend upon larger volume doses. However, there remains a need for an automatic injection device suitable for different volume doses and/or a wider range of dose volumes.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes an automatic injection device comprising a housing, a syringe, a plunger, and a syringe carrier. The housing includes a first end, a second end, and a barrel between the first end and the second end. The barrel includes an elongated window to allow viewing of contents inside the housing. The syringe is disposed within the housing and has a first end, a second end, and a reservoir therebetween. The plunger is at least partially disposed within the syringe and includes a visual indicator disposed on a portion of the plunger. The syringe carrier is disposed within the housing and configured to contain the syringe and displace the syringe within the housing between a first position and a second position. The syringe carrier can have at least one opening and at least one pair of legs defining at least a portion of the at least one opening.

For example and as embodied here, the at least one opening can be configured to align with the reservoir when the syringe carrier is in the first position. The at least one opening can include a first opening and a second opening, and the at least one pair of legs can define at least a portion of the first opening. The first opening can be configured to align with the window and the reservoir when the syringe carrier is in the first position, and the second opening can be configured to align with the window and the visual indicator when the syringe carrier is in the second position. For example, if a window is provided on a front and a rear of the housing, then corresponding first and second openings can be provided on the front and rear of the syringe carrier, respectively.

The syringe carrier can include a middle portion between the first and second openings, and the middle portion can be sized to resist deformation of the syringe carrier. The pair of legs can extend from the middle portion of the syringe carrier, and each leg can be tapered with a greater cross-dimension proximate the middle portion of the syringe carrier.

Furthermore and as embodied here, each leg of the at least one pair of legs can include an anchor portion to engage the at least one interior stop to prevent movement of the syringe carrier toward the injection site. The anchor portion of each leg can project radially outwardly. The anchor portion can include at least one or more projections sized to prevent movement of the syringe carrier toward the injection site and/or away from the injection site.

In some embodiments, the at least one pair of legs can include a first pair of legs and a second pair of legs, and the first elongated opening can include a front opening portion and a rear opening portion. The first pair of legs can define at least a portion of the front opening portion, and the second pair of legs can define at least a portion of the rear opening portion.

Additionally and as embodied here, the autoinjection device includes a liquid beneficial agent in the reservoir. The syringe carrier can be configured to allow viewing of substantially all of the liquid beneficial agent in the reservoir when the syringe carrier is in the first position. For example and not limitation, the liquid beneficial agent can have a volume of 0.4 mL. Alternatively, in some embodiments, the liquid beneficial agent can have a volume of 0.8 mL. The liquid beneficial agent can include a protein. In some embodiments, the liquid beneficial agent can include a TNF inhibitor or the like, such as adalimumab.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 1A is a front view of the automatic injection device according to an illustrative embodiment of the disclosed subject matter.

FIG. 1B is a cross-sectional side view taken along line B-B of FIG. 1A.

FIG. 2 is a perspective view of the automatic injection device of FIG. 1 according to an illustrative embodiment of the disclosed subject matter.

FIG. 3A is a front view of a syringe housing assembly of automatic injection device of an embodiment of the disclosed subject matter in a pre-injection stage, shown without the plunger for purpose of clarity.

FIG. 3B is a cross-sectional side view taken along line B-B of FIG. 3A.

FIG. 4A is a front view of the syringe housing assembly of FIG. 3A during an initial stage of operation with the stepped shroud depressed against an injection site.

FIG. 4B is a cross-sectional side view taken along line B-B of FIG. 4A.

FIG. 5A is a front view of the syringe housing assembly of FIG. 3A at the end of the injection stage with the stepped shroud pressed against the injection site.

FIG. 5B is a cross-sectional side view taken along line B-B of FIG. 5A.

FIG. 6A is a front view of the syringe housing assembly of FIG. 3A in a post-injection stage with the shroud deployed.

FIG. 6B is a cross-sectional side view taken along line B-B of FIG. 6A.

FIG. 10A is a perspective view of an embodiment of the activation button cap of the firing mechanism assembly of FIG. 9.

FIG. 10B is a cross-sectional side view of the activation button cap of FIG. 10A.

FIG. 11A is a perspective view of an embodiment of the firing body of the firing mechanism assembly of FIG. 9.

FIG. 11B is a front view of the firing body of FIG. 11A.

FIG. 12A is a perspective view of an embodiment of the plunger of the firing mechanism assembly of FIG. 9.

FIG. 12B is a front view of the plunger of FIG. 12A.

FIG. 12C is a detail view of region C of FIG. 12B.

FIG. 14A is a perspective view of an embodiment of the syringe carrier of the syringe housing assembly of FIG. 13.

FIG. 14B is an exploded view from a different perspective of the syringe carrier of FIG. 14A, including an exemplary damping structure according to an illustrative embodiment of the disclosed subject matter.

FIG. 14C is a front view of the syringe carrier of FIG. 14A.

FIG. 14D is a side view of the syringe carrier of FIG. 14A.

FIG. 14E is a cross-sectional side view taken along line E-E of FIG. 14B.

FIG. 14F is a cross-sectional front view taken along line F-F of FIG. 14D.

FIG. 14G is a cross-sectional top view taken along line G-G of FIG. 14B.

FIG. 14H is a cross-sectional side view taken along line H-H at a bottom portion of FIG. 14G.

FIG. 14I is a bottom view of the syringe carrier damper of FIG. 14B.

FIG. 14L is a cross-sectional side view of the syringe housing assembly of FIG. 13 illustrating further details of the interaction between the syringe carrier of FIG. 14A and the housing.

FIG. 14M is a detail view of region M of the FIG. 14L.

FIG. 14N is a cross-sectional side view of the syringe housing assembly of FIG. 13 illustrating further details of the interaction between the syringe carrier of FIG. 14A and the housing.

FIG. 14O is a detail view of region O of FIG. 14N.

FIG. 14P is a cross-sectional side view of the syringe housing assembly of FIG. 13 illustrating further details of the interaction between the syringe carrier of FIG. 14A and the housing.

FIG. 14Q is a detail view of region Q of FIG. 14P.

FIG. 15A is a perspective view of an embodiment of the housing of the syringe housing assembly of FIG. 13.

FIG. 15B is a front view of the housing of FIG. 15A.

FIG. 15C is a top view of the housing of FIG. 15A.

FIG. 15D is a cross-sectional front view of the housing of FIG. 15A.

DETAILED DESCRIPTION OF THE PREFERRED EMBODIMENT

Figure 7:
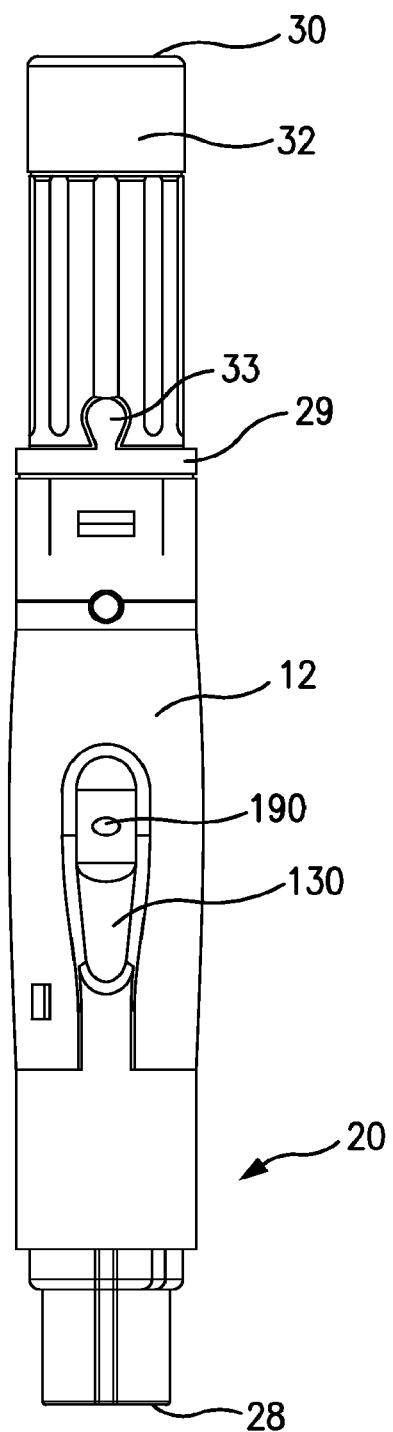
FIG. 7 is a front view of an automatic injection device similar to that of FIG. 1, but having a bulbous housing and showing the device in the post-injection stage with the indicator visible in the window.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

The apparatus and methods presented herein can be used for injecting any of a variety of suitable therapeutic agents or substances, such as a drug, into a patient. In one embodiment, the automatic injection device can be configured in the form of a pen, i.e., an autoinjector pen or autoinjection pen (used interchangeably herein). As used herein, an "automatic injection device" or "autoinjector" (used interchangeably herein) is intended to refer generally to a device that enables an individual (also referred to herein as a user or a patient) to self-administer a dosage of a liquid substance, such as a therapeutic agent, including a formulation in liquid form, wherein the device differs from a standard syringe by the inclusion of a mechanism for automatically delivering the medication to the individual by injection when the mechanism is activated. In some embodiments, the liquid therapeutic agent can include one or more biological agents, such as a protein. For example and without limitation, one such liquid therapeutic agent can be a TNF inhibitor, such as adalimumab. Additional details regarding possible therapeutic agents, including adalimumab, are provided in U.S. patent application Ser. No. 12/074,704, the contents of which are incorporated by reference herein in its entirety.

In accordance with the disclosed subject matter herein, the automatic injection device generally includes a housing, a syringe, a plunger, and a syringe carrier. The housing includes a first end, a second end, and a barrel between the first end and the second end. The barrel includes an elongated window to allow viewing of contents inside the housing. The syringe is disposed within the housing and has a first end, a second end, and a reservoir between the first end and the second end. The plunger is at least partially disposed within the syringe and includes a visual indicator on a portion of the plunger. The syringe carrier is disposed within the housing and configured to contain the syringe and displace the syringe within the housing between a first position and a second position. The syringe carrier can have at least one opening and at least one pair of legs defining at least a portion of the at least one opening.

The syringe carrier can further have one or more openings configured to align with the window and the reservoir when the syringe carrier is in the first position, and/or to align with the window and the visual indicator when the syringe carrier is in the second position.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the automatic injection device in accordance with the disclosed subject matter are shown in FIGS. 1A-19. While the present disclosed subject matter is described with respect to using the device to provide a subcutaneous injection of a dose of a TNF inhibitor, one skilled in the art will recognize that the disclosed subject matter is not limited to the illustrative embodiment, and that the injection device can be used to inject any suitable substance into a user. In addition, the components and the method of using the automatic injection device are not limited to the illustrative embodiments described or depicted herein.

Generally, and unless otherwise noted, the term "first end" refers to the portion or end of an automatic injection device or component in the automatic injection device to be disposed or positioned at or near to an injection site when the device is held against a person for an injection or for mimicking an injection. The term "second end" refers to the portion or end of an automatic injection device or a component of the automatic injection device spaced from an injection site during an injection.

Referring to an illustrative embodiment of FIGS. 1A-1B and 2, an automatic injection device 10 includes a housing 12, at least for housing a container, such as a syringe or cartridge, containing a dose of a substance to be injected into a patient. As described further below, the housing 12 embodied herein includes a first housing component 12a for housing a syringe housing assembly 121 and a second housing component 12b for housing a firing mechanism assembly 122. The housing 12 generally has a tubular configuration, though one skilled in the art will recognize that the housing 12 can have any number of suitable shapes and configurations for housing a syringe or other container of a substance to be injected. While the disclosed subject matter will be described with respect to a syringe mounted in the housing 12, one skilled in the art will recognize that the automatic injection device 10 can employ other suitable containers for storing and dispensing a substance. For example, the container for storing and dispensing a substance can be a cartridge. Additionally, the container, whether a syringe 12 or cartridge, can be made of glass, a polymer, or a variety of other suitable materials for storing and dispensing a substance.

Referring to FIGS. 1A-1B, the syringe is preferably slidably mounted in the housing 12, as described in detail below. In an inactivated position, the syringe is sheathed and retracted within the housing 12. When the device is actuated, the syringe is extended such that a needle of the syringe projects from a first end 20 of the housing 12 to allow ejection of a substance from the syringe into a patient. As shown, the first end of the housing 20 includes an opening 28 through which the needle of the syringe projects during actuation of the device 10.

Continuing to refer to FIGS. 1A-1B and 2, a firing mechanism assembly 122 is disposed in housing 12 and includes an activation button 32, exposed through a second end 30 of the housing 12, for actuating the syringe to move from the sheathed position within the housing 12 to a projecting position with the needle projecting from the housing and/or expel the substance from the syringe needle into the patient. The housing 12 can house one or more actuators to perform the function of moving the syringe and expelling the substance from the syringe.

The illustrative automatic injection device 10 shown in FIGS. 1A-1B, 2 can also include a needle shroud cap 24, as shown for example in FIGS. 17A-17D, to cover the first end 20 of the housing 12, and thus prevent exposure of or access to the needle in the syringe prior to use. In the illustrative embodiment, the needle shroud cap 24 can include a boss or hub 26 for locking and/or covering the interior components of the device 10 until the user is ready to activate the device 10. Alternatively, the needle shroud cap 24 can comprise a threaded screw portion and the first end 20 of the housing 12 at opening 28 can comprise mating screw thread. Alternative suitable mating or coupling mechanisms can be used in accordance with the teachings of the disclosed subject matter. As shown for example in FIGS. 10A-10B and discussed further below, an actuator cap 34 can also be provided to cover the second end 30 of the housing 12 and thus prevent accidental actuation of the activation button 32.

In the illustrative embodiment of FIGS. 1A-1B and 2, and with reference to FIGS. 10A-10B and 17A-17D, the housing 12 and caps 24 and 34 can further include graphics, symbols and/or numbers to facilitate use of the automatic injection device 10. For example, the housing 12 can include an arrow or other indicia on an outer surface pointing towards the first end 20 of the device to indicate the direction in which the device 10 should be held relative to the injection site. In addition, the needle shroud cap 24 can be labeled with a "1" to indicate that a user should first remove the needle shroud cap 24 of the device first, and the actuator cap 34 can be labeled with a "2" to indicate that the actuator cap 34 should be removed second after the needle shroud cap 24 is removed during preparation for and subsequent injection using the illustrative automatic injection device 10. Furthermore, either or both caps 24, 34 can be labeled with one or more arrows indicating the direction of removal. Additionally, the needle shroud cap 24 can be a different color than actuator cap 34, and labels, such as numbers and/or arrows can be accented with a highlighted or contrasting color from the corresponding cap 24, 34, such as white, to allow the user to more easily identify the caps 24, 34 and understand the sequence of removal of caps 24, 34 for preparation of the device 10. Further, the needle shroud cap 24 and/or the actuator cap 34 can include one or more contours or indentations 23, 25 sized and shaped to facilitate gripping and removal of the caps 24, 34 by the user. One skilled in the art will recognize that the automatic injection device 10 can have additional or alternative suitable graphics, symbols and/or numbers to facilitate user instruction, or the automatic injection device can omit such graphics, symbols and/or numbers.

As illustrated in FIGS. 1A-1B and 2, the housing 12 embodied herein includes at least one elongated window 130 to allow a user to view the contents of the syringe housed within the housing 12, as described in detail below. The window 130 can comprise an opening in the sidewall of the housing 12, and/or can comprise a translucent or transparent material in the housing 12 to allow viewing of the interior of the device 10. A second window can be provided diametrically opposite the first window to allow viewing through the housing and syringe if desired. Additional or alternative window embodiments likewise can be provided, for example and as further described below, wherein the window 130 is sufficient in length to function as described herein.

The housing 12 can be formed of any suitable surgical or medical device material, including, but not limited to, plastic and other known materials.

As previously noted and described in further detail below, the automatic injection device 10 disclosed herein generally comprises two components, a syringe housing assembly 121 and a firing mechanism assembly 122. For purpose of illustration and not limitation, reference is first made to the sequence of operation of the automatic injection device 10, and particularly to the operation of the syringe housing assembly 121 of the disclosed subject matter.

FIGS. 3A-6B are front and cross-sectional side views of interior components of a syringe housing assembly 121 for an automatic injection device 10 according to one embodiment of the disclosed subject matter. As shown, a syringe 50 or other suitable container for a substance is disposed within the interior of the housing 12. The illustrative syringe 50 includes a hollow barrel portion 53 for holding a dose of a liquid substance to be injected. The illustrative barrel portion 53 is substantially cylindrical in shape, though one skilled in the art will recognize that the barrel portion 53 can have a variety of suitable shapes or configurations. A seal, illustrated as a bung 54, substantially seals the liquid substance within the barrel portion 53. The syringe 50 can further include a hollow needle 55 connected to and in fluid communication with the barrel portion 53, through which the dose of liquid substance can be ejected by applying pressure to the bung 54. The hollow needle 55 extends from a first end 53a of the barrel portion 53. The second end 53b of the barrel portion 53 can include a flange 56, or other suitable mechanism, for abutting a stop, represented schematically as 123, in the housing 12 to limit the movement of the syringe 50 within the housing 12, as described below. One skilled in the art will recognize that the disclosed subject matter is not limited to the illustrative embodiment of the syringe 50 and that other suitable containers for containing a dose of a substance to be injected can be used in accordance with the disclosed subject matter. In the illustrative embodiment of FIGS. 3A-6B, the needle 55 can be a fixed twenty-seven gauge one-half inch needle. The tip of the illustrative hollow needle 55 can include five bevels to facilitate insertion. However, the needle 55 can have any size, shape and configuration suitable for the intended use as known in the art and is not limited to the illustrative embodiment. The automatic injection device 10 further includes a syringe actuation component to selectively move and/or actuate the syringe 50 to inject the dose of liquid substance contained in the syringe 50 into a user. As embodied herein, the syringe actuation component is a plunger 700 (shown in FIG. 9) and forms a part of the firing mechanism assembly 122. The plunger 700 can further have an indicator 190 (shown in FIG. 7) to indicate completion of the injection, as discussed below.

FIGS. 3A-6B illustrate the syringe housing assembly 121 in various stages of operation. In a pre-injection position, as shown in FIG. 3A, the syringe 50 is in a sheathed position within the housing 12. The needle shroud cap 24 is disposed on the first end 20 of the housing 12 to prevent access to or exposure of the needle 55. As evident from FIG. 3A, the contents of the syringe 50 are visible through the window 130. FIGS. 4A-4B illustrate the syringe housing assembly 121 in an initial stage of deployment, showing a transition between the pre-injection position and the post-injection position. At this initial stage, the stepped shroud 12d is depressed against the injection site, and the syringe carrier 700 has moved relative the window 130 toward the first end 20 of the housing 12. FIGS. 5A-5B show the syringe housing assembly 121 at the end of the injection stage with the stepped shroud 12d still depressed against the injection site, such that the needle 55 is extending from the housing 12 into the injection site. Upon completion of the stroke or movement of the syringe 50, the contents of the syringe 50 are no longer visible through the window 130. As described herein, however, the indicator 190 on the plunger or actuation component 700 will then be visible for indication that injection is complete and that the device 10 can be removed from the injection site. FIGS. 6A-6B show the syringe housing assembly 121 in the post-injection position, with the device 10 removed from the injection site causing the stepped shroud 12d to deploy, as further described below. As described herein, the indicator 190 on the plunger or actuation component 700 remains visible to indicate that the device has been deployed.

Figure 8:
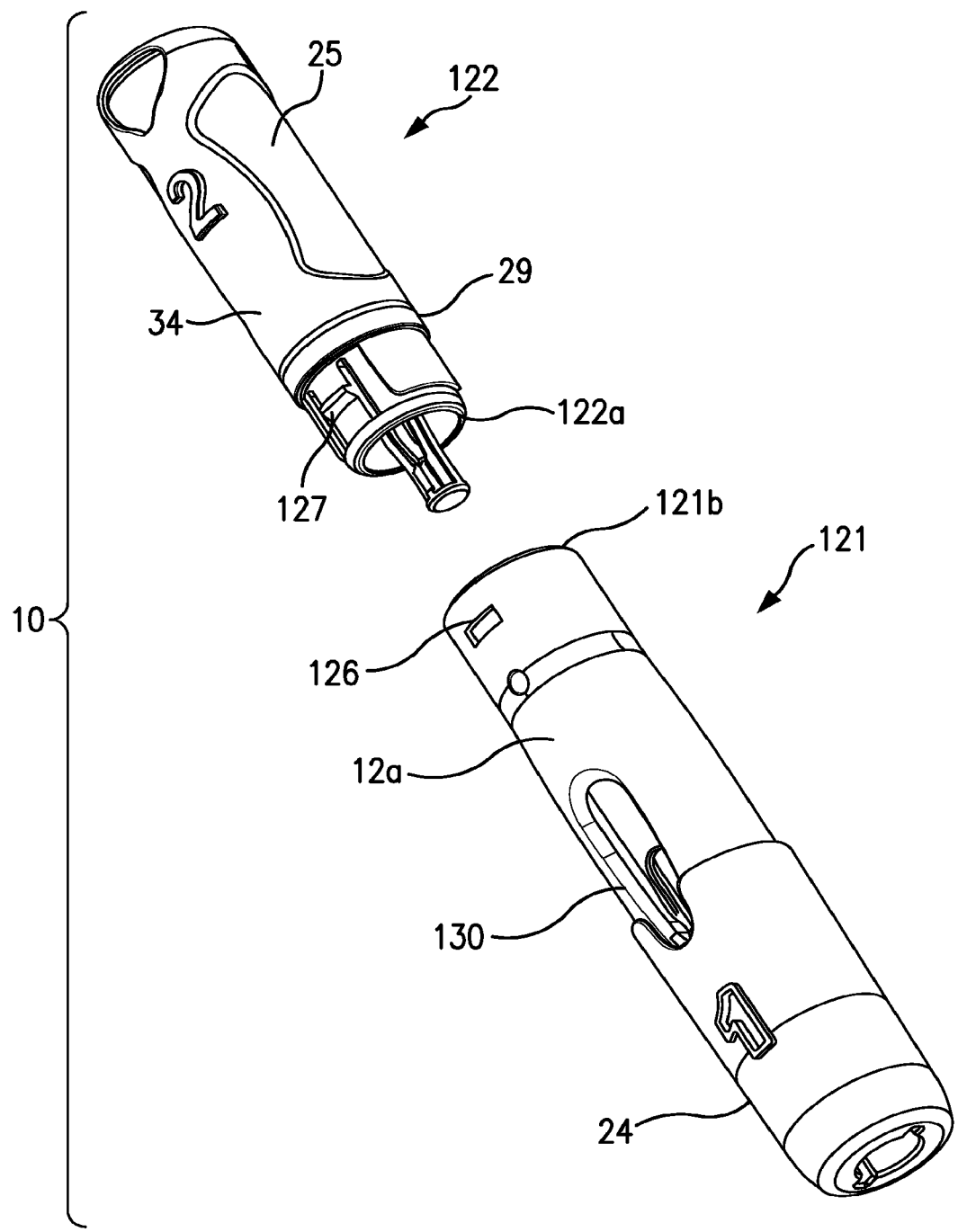
FIG. 8 is an exploded perspective view of an embodiment of an automatic injection device according to one embodiment of the disclosed subject matter.

As previously noted, and with reference to FIG. 8, the automatic injection device 10 can comprise two interlocking components: a syringe housing assembly 121 and a firing mechanism assembly 122. The syringe housing assembly 121 and the firing mechanism assembly 122 can be coupled through any suitable means. In the illustrative embodiment, a first end 122a of the firing mechanism assembly 122 can be sized and configured to be inserted into a second end 121b of the syringe housing assembly 121. In addition, one or more tabs 127 on the first end 122a of the firing mechanism assembly 122 can snap-fit into corresponding openings 126 on the second end 121b of the syringe housing assembly 122 to ensure alignment and coupling of the two assemblies 121, 122 and the components housed therein.

Figure 9:
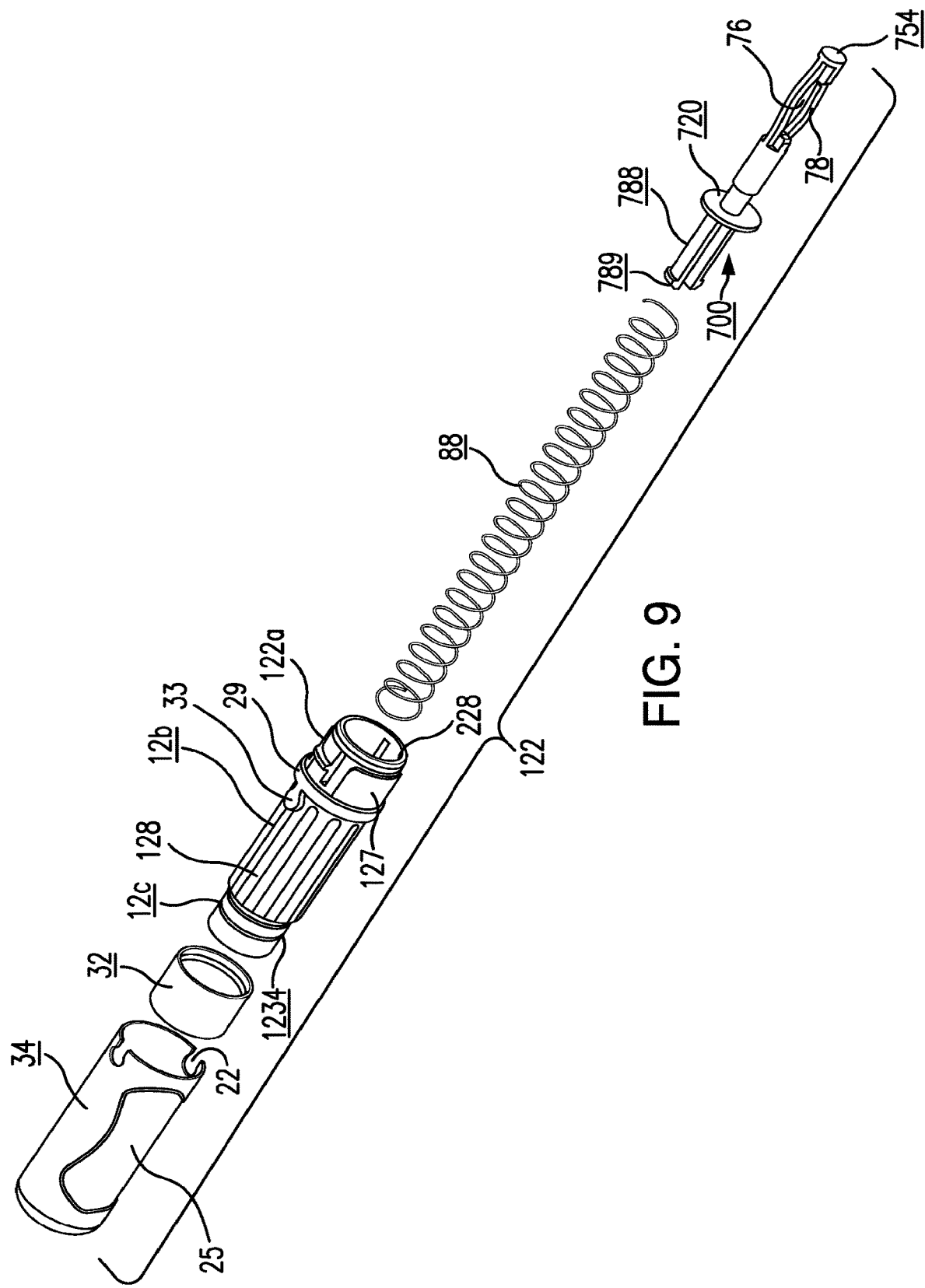
FIG. 9 is an exploded perspective view of an embodiment of the firing mechanism assembly of the automatic injection device of FIG. 8 according to an illustrative embodiment of the disclosed subject matter.

FIG. 9 is an exploded view of the firing mechanism assembly 122, for illustration and not limitation, according to a representative embodiment of the disclosed subject matter. As shown, the firing mechanism assembly 122 includes an activation button 32, an actuator cap 34, housing component 12b (firing body) and a coil spring 88 or other biasing mechanism. The illustrative firing mechanism assembly 122 further includes a syringe actuator, such as a syringe actuation component 700, that extends from the first end 122a of the housing component 12b. As embodied herein, the syringe actuation component 700 can be configured to move the syringe 50 in a first phase and actuate the syringe 50 to expel its contents in a second phase.

FIGS. 10A-10B illustrate the actuator cap 34 according to illustrative embodiments of the disclosed subject matter. The actuator cap 34 can include a locking pin 36 to engage the activation button 32 and prevent inadvertent actuation of the activation button 32 before actuator cap 34 is removed. The actuator cap 34 can be mounted on the housing in a variety of ways. For example, and as shown in FIG. 9, the second end of the housing 12 can be provided with a diameter smaller than the an adjacent section of the housing. A step 29 can be formed at the transition between the two diameters to facilitate seating of the actuator cap 34 on the second end 30 of the housing.

The actuator cap 34 can have a distinctive color to differentiate the first end 20 and second end 30 of the device, though one skilled in the art will recognize that the actuator cap 34 and housing 12 can have any suitable color, size and configuration.

As shown in FIGS. 1A-1B and 10A-12B, the firing body 12b includes a substantially tubular body, which can include taper and/or contours 128 to facilitate gripping of the device 10 by a user. A step 29 can be formed in a second end 30 to facilitate seating of the actuator cap 34, as described above. Additionally, a mating feature can be provided to secure the actuator cap 34 to the firing body 12b. For example, and as depicted in FIG. 9, mating tabs 33 on the firing body 12b can be configured to be received within receptacles 22 of actuator cap 34, for example by an engagement or snap-fit or the like, and thus lock the actuator cap 34 to the firing body 12b and activation button 32 and prevent inadvertent removal of the actuator cap 34. Mating tabs 33 can also align actuator cap 34 with the housing 12 during assembly and prevent rotation of the actuator cap 34 relative to the firing body 12b during transportation or handling of the device 10, which can prevent accidental firing of the device 10. As embodied herein, the mating tabs 33 and corresponding receptacles 22 can have a petal shape, although other configurations can be used. Forward of the step 29, the firing body 12b has a size and shape configured to be inserted into the distal end of the syringe housing 121. Tabs 127 are formed to facilitate coupling and/or locking of the two housing components 12a and 12b together. As shown in FIGS. 11A-11B, the tabs 127 can be formed in a depression 127a on the surface of the proximate end of the firing body 12b, and can also or alternatively include ribs 127b for guiding the tabs into a locking position relative to the proximate housing component 12a. One skilled in the art will recognize that any suitable means for coupling the two assemblies together can be used and that the invention is not limited to the illustrative coupling means.

As shown in FIGS. 11A-11B, the firing body 12b can include an anchoring cap 12c coupled to a smaller diameter distal end of the firing body 12b for anchoring the firing mechanisms for actuating the device 10 to the firing body 12b. The interface of the anchoring cap 12c and the firing body 12b can form a groove 1234 to facilitate a snap fit of the activation button 32 on the distal end of the firing body 12b, or can be joined by other suitable joining means as described above.

Referring to FIGS. 3B and 12A-12C, the syringe actuation component 700 can be an integrated component formed of any suitable material, such as an acetal-based plastic, though other suitable materials can also be used. The syringe actuation component 700 comprises a pressurizer 754 for applying pressure to the bung 54 of a corresponding syringe 50, and a plunger rod portion 70 with a compressible expanded central portion, illustrated as the plunger elbows 78. Additional components, such as components for anchoring the coil spring 88 to the syringe actuation component 700, can also be provided as described below. The compressible expanded central portion 76 facilitates movement of a corresponding syringe 50 toward the injection site and expulsion of the contents of the syringe 50 in two separate steps, as described above. Alternatively, the syringe actuator can comprise multiple actuators for moving and/or promoting expulsion of the syringe 50.

The syringe actuation component 700 of FIGS. 3B and 12A-12C can further include an indicator 190 in a solid rod portion 70 distal from the elbows 78. During operation of the device 10 and after completion of an injection, the indicator 190 is configured to align with the window 130 on the housing 12 to indicate completion of the injection. The indicator 190 preferably has a distinctive color or design to represent completion of an injection.

As shown in FIGS. 1B, 8 and 12A-12C, the illustrative syringe actuation component 700 further includes a retaining flange 720 for holding the actuating coil spring 88 in a compressed position until actuation. The retaining flange 720 is sized, dimensioned and formed of a material that preferably allows the syringe actuation component 700 to slidably and easily move within the housing 12 when the device 10 is actuated. Extending distally from the retaining flange 720, the syringe actuation component 700 forms a base 788 for the actuating coil spring 88. The base 788 terminates in a trigger anchoring portion 789. For example, and as depicted herein, the illustrative base 788 can comprise flexible legs 788a, 788b around which the spring 88 is disposed. The trigger anchoring portion 789 can comprise tabbed feet 7891 extending from the base 788 and configured to selectively engage the anchoring cap 12c and/or firing body 12b. The tabbed feet 7891 can include one or more angled surfaces to define a cam or the like. For example, and as shown in FIG. 12C, the tabbed feet 7891 can have a substantially arcuate shape formed by multiple edge segments, each having a different angle relative to the length of the base 788. As embodied herein, for purpose of illustration and not limitation, from the end of the tabbed feet 7891 towards the base 788, the edge segments can have successively decreasing angles .alpha., .beta., .gamma. of 82.degree., 45.degree. and 23.degree., respectively. The activation button 32 coupled to the distal end of the firing body 12b is configured to hold the trigger anchoring portion 789 until activation. When activated, the activation button 32 releases the trigger anchoring portion 789, allowing the spring 88 to urge the syringe actuation component 700 toward the proximal end 20 of the device 10 in an operation described above.

In a retracted, anchored position shown FIGS. 1B, 3B and 12A-12C, the trigger anchoring portion 789 interacts with the housing 12, which holds the tabbed feet 7891 in a latched position, against the biasing force of the coil spring 88, to maintain the syringe actuation component 700 in a retracted position. In this position, the flange 720 retracts the spring 88 against the back, distal wall 712 of the firing body 12b. An opening 713 in the anchoring cap 12c allows the activation button 32 access to the anchoring portion 789. In the retracted position, the pressurizer 754 of the syringe actuation component 700 extends out of an opening 228 on the proximal end 122a of the firing body 12b. When the firing body 12b couples to a corresponding syringe actuation mechanism 121, the pressurizer 754 extends into the barrel portion of a syringe housed therein. The pressurizer 754 can be integral with, the same as, connected to, or otherwise in communication with the bung 54 of a syringe 50 housed in the device 10 and can be provided with any suitable size, shape and configuration suitable for applying pressure to the bung 54. In one embodiment, the pressurizer 754 has a cross-section corresponding to the shape of the barrel portion 53 of a corresponding syringe 50 so as to substantially seal the barrel portion 53, and the pressurizer 754 is configured to slidably move within the barrel portion 53 to apply pressure to the bung 54 and actuate the syringe 50.

In the illustrative embodiment of FIG. 9, the syringe actuation component 700 constitutes a single, integrated mechanism for anchoring a corresponding syringe 50, spring 88 and other components, actuating and moving the syringe 50 to an extended position, and expelling the contents of the syringe 50. Additional details of the illustrative firing mechanism assembly 122 and related aspects of the automatic injection device 10 are provided in U.S. patent application Ser. No. 12/074,704, which is incorporated by reference herein in its entirety.

Figure 13:
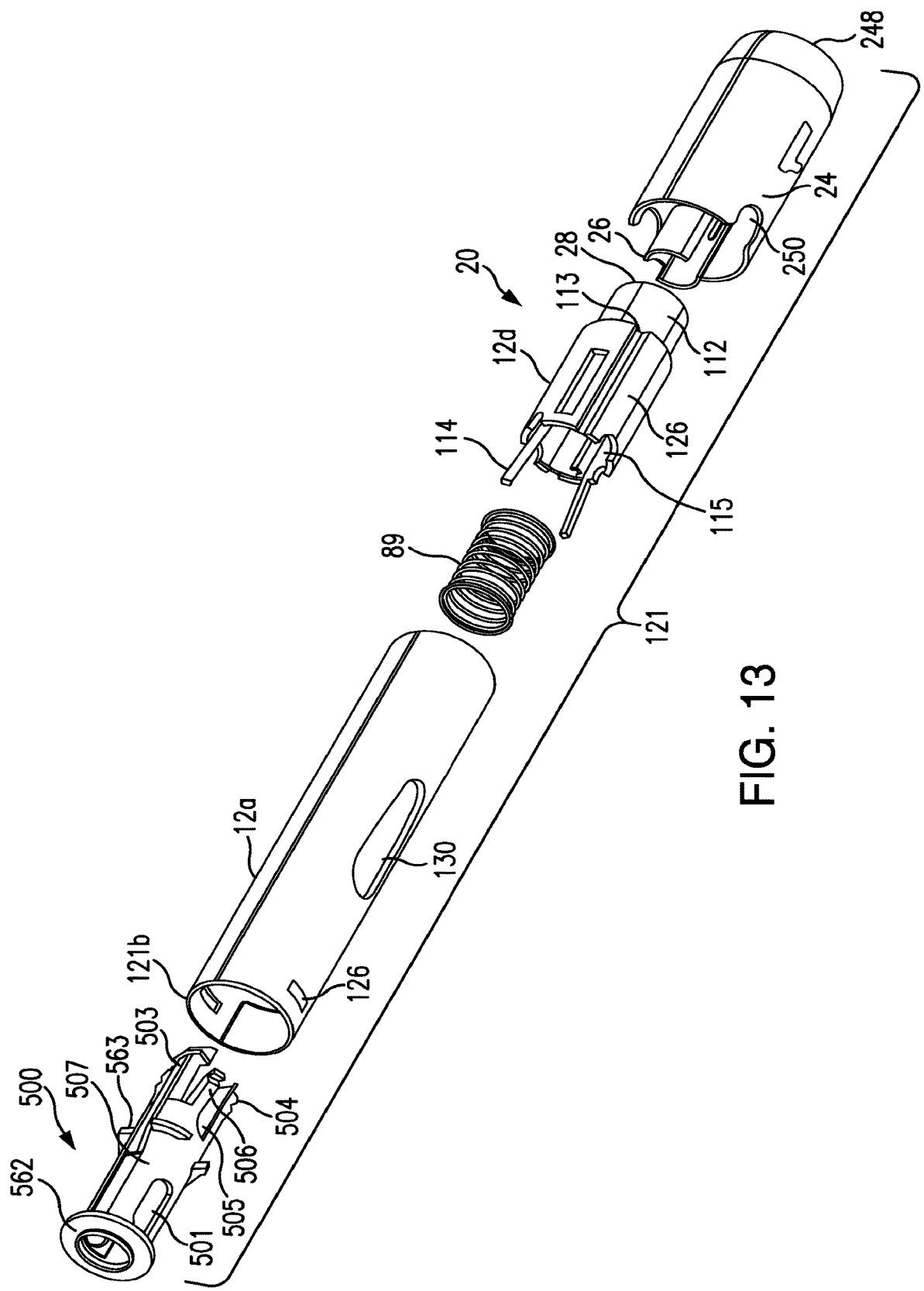
FIG. 13 is an exploded perspective view of an embodiment of the syringe housing assembly of the automatic injection device of FIG. 8 according to an illustrative embodiment of the disclosed subject matter.
Figure 14J:
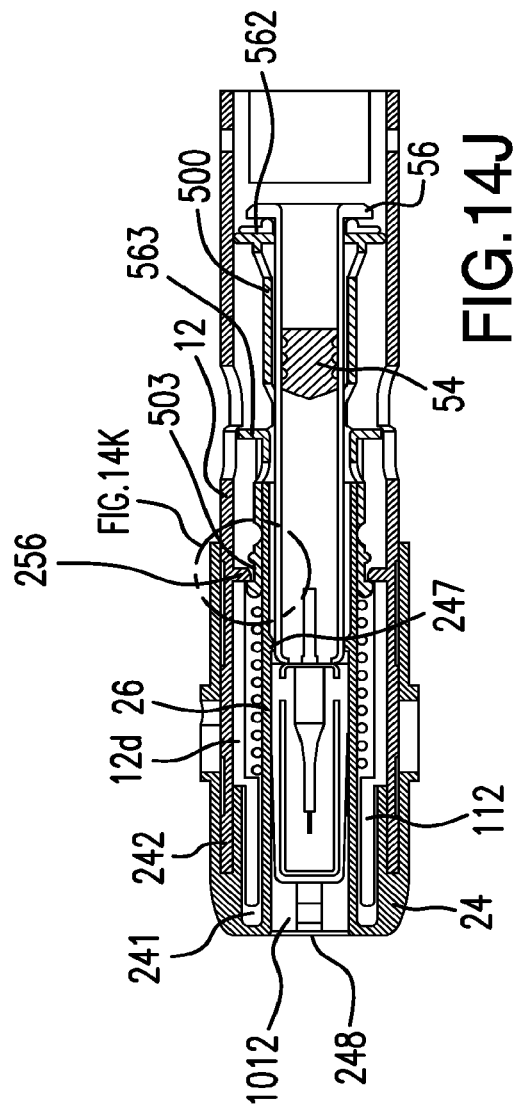
FIG. 14J is a cross-sectional side view of the syringe housing assembly of FIG. 13 illustrating further details of the interaction between the syringe carrier of FIG. 14A and the housing.
Figure 14K:
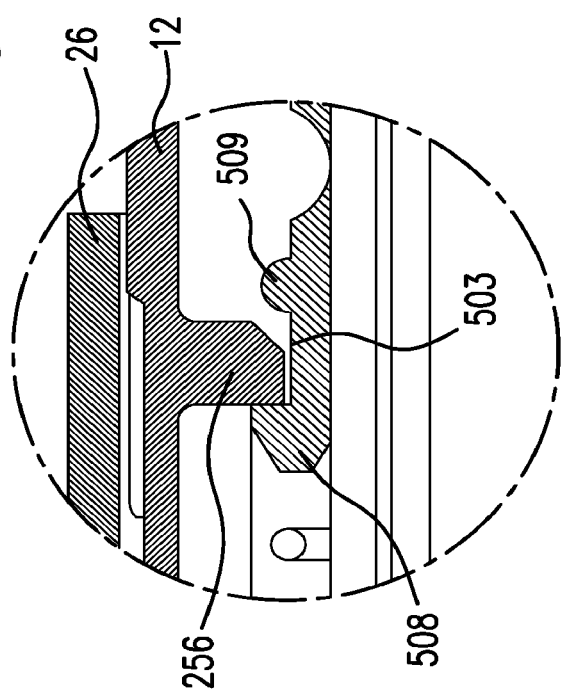
FIG. 14K is a detail view of region K of FIG. 14J.

FIG. 13 is an exploded view of the syringe housing assembly 121 of an illustrative embodiment of the disclosed subject matter, which for purpose of example and not limitation is configured to couple to and interact with the firing mechanism assembly 122 of FIG. 9. The illustrative syringe housing assembly 121 includes a housing component 12a, a needle shroud cap 24, a biasing mechanism 89, a syringe carrier 500, and a stepped shroud 12d at the first end 20 of the housing 12 when assembled and includes the first opening 28, as also shown in FIG. 7. The components 12a, 12d, 89, 500 and 24 cooperate to house a syringe 50 containing a substance to be injected and facilitate operation of the device 10 as described above. Additional details of the illustrative syringe housing assembly 121, firing mechanism assembly 122 and related aspects of the automatic injection device 10 are provided in U.S. patent application Ser. Nos. 13/443,384; 12/968,744; 12/770,557 and 12/074,704 and U.S. Pat. Nos. 8,162,887; 7,938,802; 7,229,432 and 6,805,686, each of which is incorporated by reference herein in its entirety.

Figure 18B:
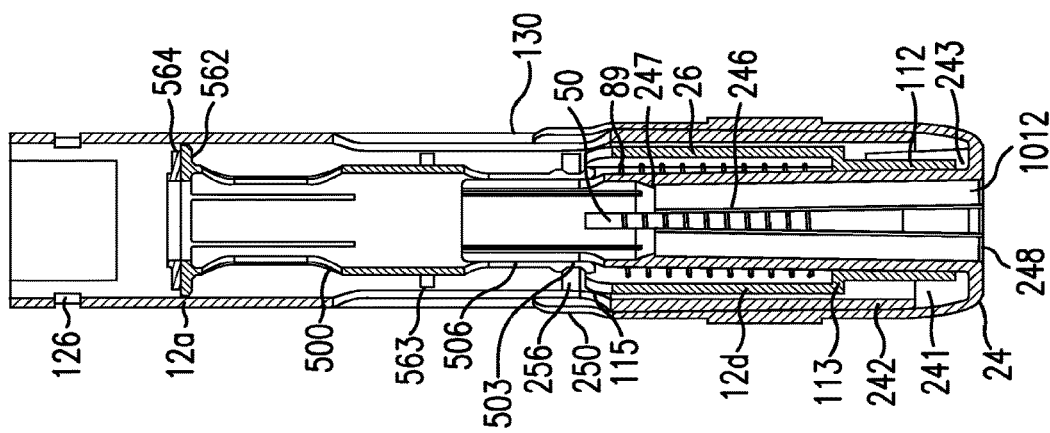
FIG. 18B is a cross-sectional side view taken along line B-B of FIG. 18A.
Figure 18A:
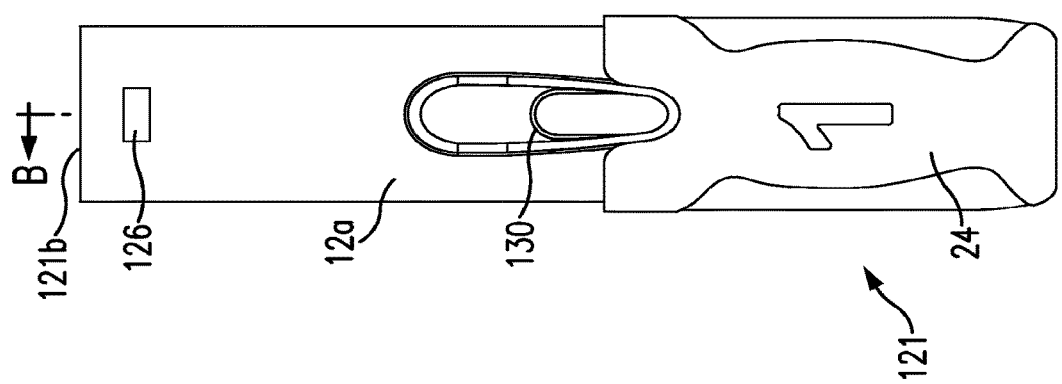
FIG. 18A is a front view of an embodiment of the syringe housing assembly of FIG. 8 according to an illustrative embodiment of the disclosed subject matter.

Illustrative embodiments of the syringe carrier 500, housing 12, the stepped shroud 12d and the needle shroud cap 24 are shown in detail in FIGS. 14A-14Q, 15A-15D, 16A-16B and 17A-17D, respectively. FIGS. 18A and 18B are a perspective side view and a cross-sectional side view, respectively, of the assembled spring housing assembly 121 according to one embodiment of the disclosed subject matter. One skilled in the art will recognize that the disclosed subject matter is not limited to the illustrative embodiments only.

Referring now to FIGS. 1A-1B, 2, 13, 14A-14Q, and 18A-18B, the syringe carrier 500 of the illustrative embodiment holds or contains at least a portion of a syringe 50 used in the device 10. The syringe 50 rests in the carrier 500, which in turn is contained in the housing 12. During operation, the syringe 50 and carrier 500 move forward (e.g., towards the first end 20 proximate the injection site) within the housing 12. The housing 12 is configured to limit the movement of the carrier 500 beyond the first end 20, and the carrier 500 in turn limits the movement of the syringe 50. The syringe carrier 500 embodied herein has a substantially tubular structure including at least a first opening 505 proximate the first end of the carrier 500 and a second opening 501 space from the first end of the carrier 500.

In accordance with another aspect of the disclosed subject matter, and with reference to the embodiment of FIGS. 14A-14I, the first opening 505 can be defined by legs 506 extending from a middle portion 507 disposed between the first opening 505 and the second opening 501. In the assembled state, the first opening 505 is located closer to the first end of the housing 12a than the second opening 501. The middle portion 507 is sized and configured to provide suitable strength to the syringe carrier 500 to prevent breaking or deformation of the syringe carrier 500 during operation of the device. Furthermore, additional openings can be provided to correspond with the window 130 or windows of the housing. For example, for either or both of the first opening 505 or second opening 501, a front opening can be provided diametrically opposite a rear opening to allow viewing through the syringe carrier 500.

For example, an as illustrated in FIGS. 14A-14Q, the legs 506 embodied herein each also include an anchor portion 503 at a first end of each leg 506. The anchor portion 503 of each leg 506 includes a first projection 508 and a second projection 509 to define a generally radial groove. In the illustrative embodiment, in the pre-injection position, the first and second projections 508, 509 engage an interior stop 256 within the radial groove, as shown in FIGS. 15C-15D and 18B. The first projection 508 can be larger than second projection 509 and sized to prevent movement of the first projection 508 past the interior stop 256, thus preventing movement of the syringe carrier away from the injection site.

As shown in FIGS. 14J-14Q, the second projection 509 can be configured to pass the interior stop 256 when the syringe carrier 500 is urged toward the injection site, as described below. The second projection 509 can be configured such that the additional force to move the second projection 509 past the interior stop 256 can be less than the force to advance the plunger 700 within the syringe, and thus prevent advancement of the plunger 700 and expulsion of the syringe contents before the syringe 50 and needle 55 are moved to the injection site. For example, and as embodied herein, the surface of second projection 509 can be substantially arcuate or include an arcuate portion configured to abut the interior stop 256, and interior stop 256 can include a chamfered edge portion configured to abut the second projection 509 to reduce the amount of force to urge the second projection 509 past the interior stop 259. Additionally or alternatively, legs 506 can act as a living hinge, which can provide for easier assembly of the syringe carrier 500 into the syringe housing assembly 121 and also allow the syringe carrier 500 to move past the interior 259.

Additionally, for purpose of illustration and not limitation, and as embodied herein, syringe carrier 500 can be configured with two pairs of legs 506 distributed substantially symmetrically about the barrel of the syringe carrier 500, which can provide substantially even distribution of the force applied to the syringe carrier legs 506 when engaging interior stops 256 of the housing 12, and thus prevent damage to legs 506 during assembly, transportation or handling. Further, force can be distributed substantially evenly to each leg 506 when a force is applied to the syringe carrier 500 to move the second projection 509 of each leg 506 past each interior stop 256 of the housing 12. In this manner, the legs 506 can be released from the housing 12 at substantially the same time for improved activation, including, for example, when syringe 50 is tilted and contacts the syringe carrier 500 at the start of the device 10 activation and firing.

A syringe carrier coupler 504, formed as two beams extending from the middle portion 507, extends forward beyond the anchor portion 503 to facilitate coupling of the syringe carrier 500 with an end of the spring 89 and/or the stepped shroud 12d.

The legs 506 are sized and shaped for added durability and strength. For example, either or both of the first and second projections 508, 509 of legs 506 can be wedge-shaped and have a thickness to provided added strength. Additionally, the legs 506 can be tapered for greater width or thickness proximate the middle portion 507, and/or the legs 506 can be angled slightly radially outward relative a longitudinal axis of the syringe carrier 500 to more securely engage the interior stop 256.

The syringe carrier 500 can include a flanged second end 562 configured to interface with a flanged second end 56 (shown in FIG. 18B) of the syringe 50. The flanged second end 562 can serve as a damper for the syringe 50. Additionally, the flanged second end 562 can include a damping structure 564, such as an elastomeric member mounted on or formed integrally with the second end 562 of the syringe carrier 500. The syringe carrier 500 can further include one or more intermediate flanges 563, which in the illustrative embodiment forms a stop for the syringe 50 to interact with an interior stop 256 on the housing component 12a to limit forward motion of the syringe 50.

As depicted herein, the syringe carrier 500 is slidably disposed within the housing 12 and selectively carries the syringe 50 within the housing 12. Alternatively, the syringe carrier 500 can be stationary within the housing 12 and configured to allow the syringe 50 to selectively and controllably slide within and relative to the syringe carrier 500. The syringe carrier 500 can have other suitable configurations and sizes for carrying or guiding the syringe 50 within the housing 12.

Figure 16B:
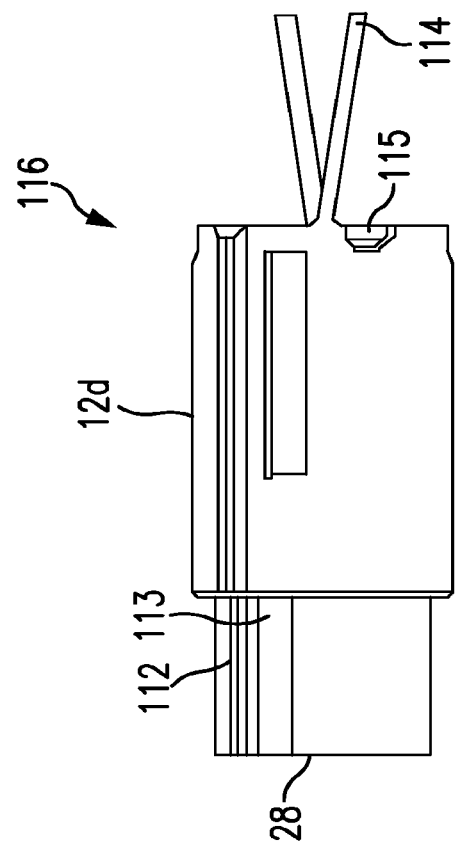
FIG. 16B is a front view of the stepped shroud of FIG. 16A.
Figure 16A:
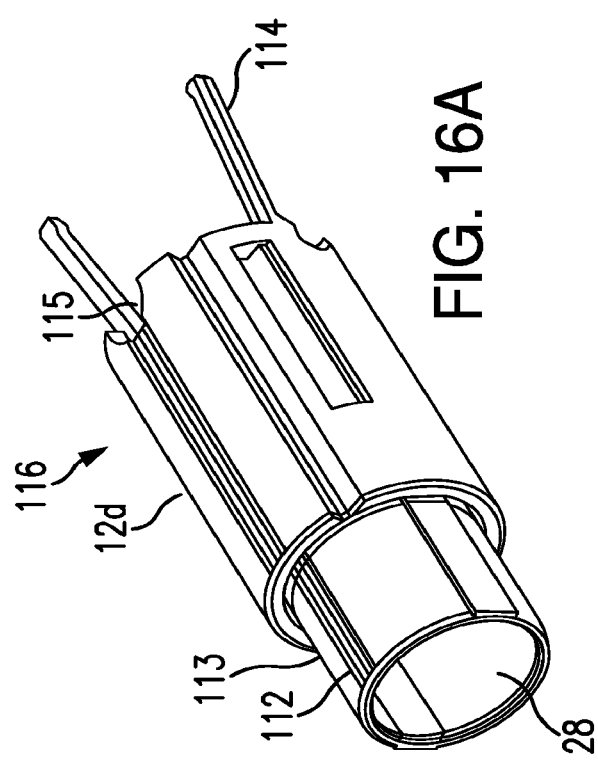
FIG. 16A is an embodiment of the stepped shroud of the syringe housing assembly of FIG. 13.
Figure 17C:
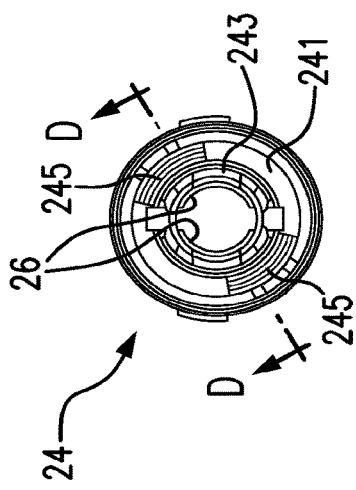
FIG. 17C is a top view of the needle shroud cap of FIG. 17A.
Figure 17D:
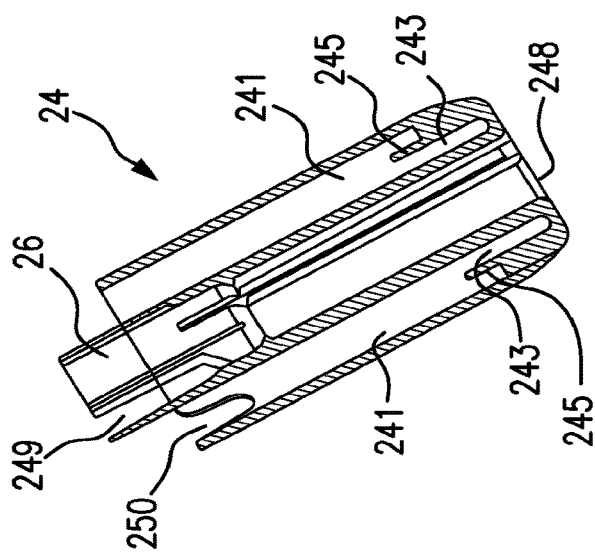
FIG. 17D is a cross-sectional side view of the needle shroud cap taken along line D-D of FIG. 17C.
Figure 17A:
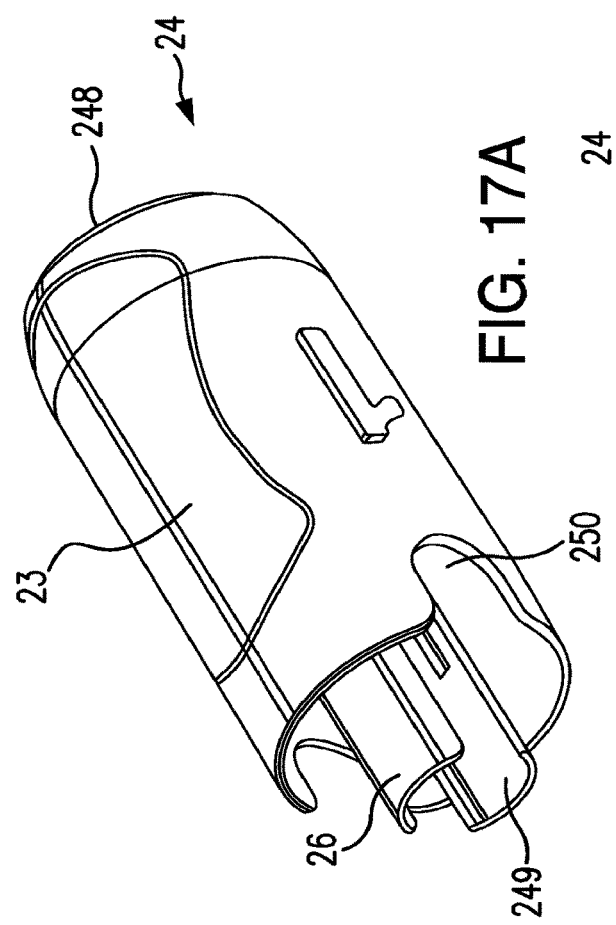
FIG. 17A is a perspective view of an embodiment of the needle shroud cap of the syringe housing assembly of FIG. 13.
Figure 17B:
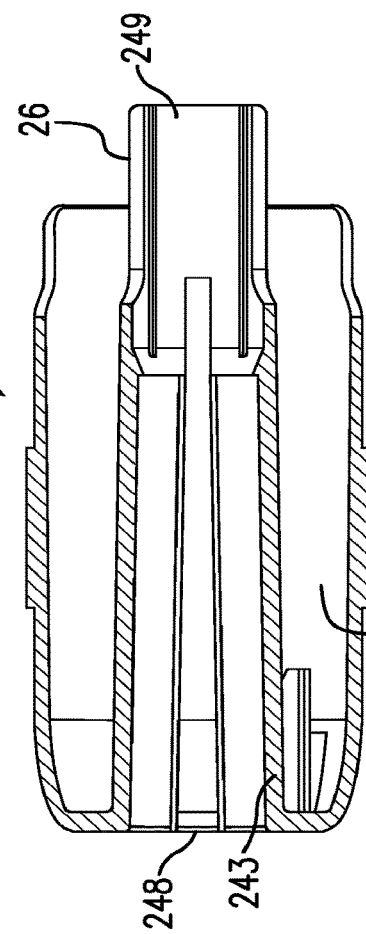
FIG. 17B is a cross-sectional front view of the needle shroud cap of FIG. 17A.

Referring to FIGS. 16A-16B and 18B, the illustrative stepped shroud 12d is disposed at the first end 20 of the housing 12. The illustrative stepped shroud 12d has a substantially tubular body, including a hub 112 defining the opening 28 at the first end 20 of the device 10, through which the syringe needle 55 can project during operation of the device 10. A step 113 from the main tubular body portion 116 forms the hub 112 of smaller diameter than the main tubular body portion 116 of the stepped shroud 12d. As shown in FIG. 18B, the step 113 forms a forward stop for the spring 89 to confine the spring 89. In the illustrative embodiment, shown in FIGS. 16A-16B and 18B, a shroud notch 115 is formed in a rim at the second end of the stepped shroud 12d. The rim of the stepped shroud 12d abuts the first side of the stop 256 of the housing component 12a. The shroud notch 115 can align with a portion of the window 130 to prevent obstruction of the window 130. Additionally, arms 114 extend from the stepped shroud 12d to lock in the stepped shroud 12d to prevent accidental needle sticks. The stepped shroud 12d can further include a guide, such as a groove and/or slot 118 as shown in FIGS. 16A-16B to receive corresponding projections or keys 257, as shown in FIGS. 15C-15D, and thus allow for coaxial movement of the stepped shroud 12d and the syringe carrier 500 without rotation relative the housing 12. The configuration and operation of the stepped shroud 12d is described further in U.S. application Ser. No. 12/074,704, and U.S. Pat. Nos. 7,229,432 and 6,805,686, each of which is incorporated by reference herein in its entirety.

Referring again to FIGS. 14A-16B and 18B and to the stages of operation of the device shown in FIGS. 3A-6B, with the device in the pre-injection position, the cap 24 is removed and the stepped shroud 12d is depressed against the injection site and thus retracted within the housing 12. Upon activation of the firing assembly mechanism 121, the syringe carrier 500 is urged forward, toward the first end of the device 10, and the legs 506 deflect radially outward causing the anchor portions 503 to disengage from the stop 256 to allow the syringe carrier 500 to move forward. As the syringe carrier 500 is urged forward, beams of the syringe carrier coupler 504 compress spring 89 and engage the second end of stepped shroud 12d. After plunger 700 is fully deployed, and completion of the injection is confirmed as described below, the device 10 can be removed from the injection site. At this point, the device is in the post-injection position with stepped shroud 12d extended beyond the needle 55 due to spring 89 and locked in the extended position by arms 114 abutting the stop 256.

Referring to FIGS. 17A-17D and 18A-18B, the interior of the illustrative needle shroud cap 24 can include a plurality of radial grooves 241, 243 for receiving protruding portions of the stepped shroud 12d and the housing component 12a. For example, as illustrated in FIG. 18B, a first radially outer groove 241 receives a first end of the sidewall 242 of the housing component 12a. A second, radially inner groove 243 receives the first end of the hub 112 of the stepped shroud 12d. The second end of needle shroud cap 24 includes a cap notch 250 to align with a portion of the window 130 to prevent obstruction of the window 130 when the needle shroud cap 24 receives the housing 12 (as best shown in FIGS. 3A-3B). The radial grooves 241, 243 can be separated by a radial inner wall 245, which can be formed as a ring, or alternatively can be formed as a plurality of arcuate wall portions.

The needle shroud cap 24 further includes a cap hub 26. Cap hub 26 is configured to extend into the inner lumen 1012 of the housing 12 and surround the first end of a syringe 50 loaded therein when the needle shroud cap 24 is coupled to the housing 12. The cap hub 26 can include two or more members, if desired, to define a hub opening 249. When the needle shroud cap 24 receives the housing 12, the hub opening 249 can align with the at least a portion of the window 130 to prevent obstruction of the window by the cap hub 26. Additionally, and as shown in FIG. 18B, a second end of the cap hub 26 can be configured with a reduced thickness to fit between syringe 50 and the first end of legs 506. In this manner, the legs 506 are radially deflected inward into engagement with the housing stop 256 to prevent premature deployment of the stepped shroud 12d when the cap 24 is removed.

As embodied herein, a separate interior needle cover 246 (shown in FIG. 1B), such as a conventional rigid needle shield, sheaths the syringe needle 55. When the cap 24 is placed onto the housing 12, a circumferential ridge 247 can engage and secure the interior needle cover 246 within the cap 24. When the cap 24 is removed, the syringe needle 55 is exposed within the lumen 1012 of the housing 12. The cap 24 can also include an opening in a first end 248 thereof. The cap 24 can further include one or more slots or apertures in a side thereof to allow for expansion of the radial grooves 241, 243 or the hub 26 and/or to facilitate the needle cover 246 passing the circumferential ridge 247 when the cap 24 is placed onto the housing 12.

Referring again to the stages of operation of the automatic injection device 10 shown in FIGS. 3A-6B, the alignment of the openings 501, 505 of the syringe carrier 500 with the window 130 and other components of device 10 is described. In the pre-injection position shown in FIGS. 3A-6B, the first opening 505 of the syringe carrier 500 in the first position is aligned with the window 130, the cap notch 250, and the shroud notch 115. This alignment allows viewing of the syringe barrel 53 through the window 130 to permit viewing of the contents of the syringe 50. In the initially deployed position shown in FIGS. 4A-4B, the middle portion 507 of the syringe carrier 500 is visible in the window 130, along with portions of the first opening 505 and the second opening 501. The shroud notch 115 can be aligned with the window 130 if the shroud 12d is pressed against the injection site. This alignment can indicate that the device 10 is currently in operation. At the end of the injection, shown in FIGS. 5A-5B, the second opening 501 of the syringe carrier 500 is in the second position and aligned with the window 130 and the indicator 190 of the syringe actuation component 700 to indicate that the injection is completed. The shroud notch 115 can be aligned with the window 130 if the shroud 12d is pressed against the injection site. In the post injection position, shown in FIGS. 6A-6B, with the shroud 12d deployed, the second opening 501 of the syringe carrier 500 in the second position remains aligned with the window 130 and the indicator 190 of the syringe actuation component 700 to indicate that the device 10 has been deployed, as described further.

As described above and shown in FIG. 18A, openings 126 in the housing component 12a receive tabs 127 of the firing mechanism assembly 122 to facilitate assembly of the device 10. The window 130 described above for allowing a user to view the contents of a syringe contained in the assembly 121, as well as to view an indicator 190 that fills the window 130 after completion of an injection can be formed only in the first housing component 12a if sufficient length is available to function as described.

With reference now to the indicator 190, FIG. 7 is a front view of the automatic injection device 10 of an embodiment of the disclosed subject matter, illustrating the syringe actuation component 700 according to one embodiment of the disclosed subject matter. The syringe actuation component 700 can form or otherwise include an indicator 190 visible through the window 130. The indicator 190 can be provided with a distinctive color, shape, and/or design to indicate to a user that an injection is complete. The indicator 190 is configured to align with the window 130 of the housing 12 after the syringe actuation component 700 completes an injection and fully or substantially fully expels the contents of the syringe 50 out of the needle 55 and into a patient. Thus, prior to operation of the device 10, the syringe barrel 53 aligns with the window 130 and the contents are viewable therein through the first opening 505 of the syringe carrier 500 in its first position. After injection, the syringe barrel portion 53 has moved towards the first end 20 of the device 10, such that the needle 55 protrudes from the first end 20 of the housing 12, and the syringe actuation component 700 has moved forward within the syringe barrel portion 53. In this position, the indicator 190 is aligned with and visible in the window 130 through the second opening 501 of the syringe carrier 500 to indicate completion of an injection. Therefore, and in accordance with this embodiment, even when the syringe 50 has moved into an exposed position with the needle 55 protruding from the housing 12, the indicator 190 will not align with the window 130 or otherwise indicate completion of an injection until the plunger 700 has expelled the contents of the syringe 50 out of the barrel 53.

Referring to FIGS. 15A-15D, the illustrative housing 12 includes a window 130 formed in a side wall of the housing 12 to allow a user to view the contents of the syringe prior to operation and to allow a user to view the indicator 190 after the device operation is completed. As embodied herein, as shown in FIGS. 15A-15D, the illustrative window 130 preferably has an elongated shape of sufficient length for visibility of the first opening 505 of the syringe carrier 500 in the first position and the second opening 501 of the syringe carrier 500 in the second position. For example, the window 130 can have an oval shape with a first end 132 that is narrower than a second end 134, and the first end can align with a cap notch 250 when the cap 24 receives or is positioned in the housing 12. The second end 134 of the window 130 can be substantially semi-circular in shape and wider than the first end 132 of the window 130 for better visibility of indicator 190, if provided.

Figure 19:
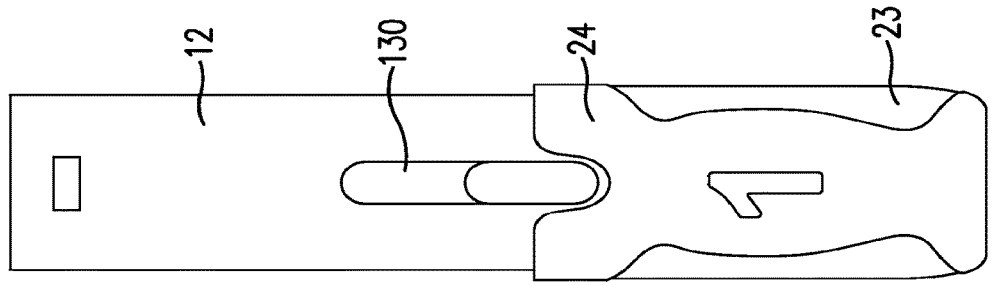
FIG. 19 is a front view of a further embodiment of the syringe housing assembly of FIG. 8 according to an illustrative embodiment of the disclosed subject matter.

FIG. 19 shows an alternate embodiment of device 10 with an alternative window 130 configuration. In contrast to the tapered or tear-drop configuration previously described, window 130 is generally oval-shaped. As shown in FIG. 19, the window 130 can have a substantially symmetrical oval shape or pill shape and can preferably be configured as an open slot, or can alternatively be configured to include a transparent window cover to protect the contents of the device 10 and allow viewing of the syringe contents therethrough, as well as to view an indicator 190 that fills the window 130 after completion of an injection. Further, the window 130 configuration of FIG. 19 can be utilized with any of the embodiments of device 10 and syringe carrier 500 described herein. The window 130 can include a fill line 135 to allow verification of the proper dosage within the syringe.

The housing 12 can also include a beveled edge 136 surrounding the window 130. The beveled edge 136 can be used to receive and secure an optional shield 137. The shield 137 can be hingedly attached to cover the window 130, if made of an opaque material, or can be made of any suitable transparent material and secured to the housing 12 to allow the user to see through the shield 137. The shield 137 can also have properties to absorb or reflect, or otherwise prevent ultraviolet or other light wavelengths from entering the housing and damaging the contents of the syringe 50. For example, the shield 137 can include a transparent protective film with properties to block or absorb ultraviolet light, and the film can also include an adhesive layer for application to the shield 137 and/or to a pre-filled syringe. Additionally or alternatively, a chemical having ultraviolet blocking or absorbing properties can be added to a transparent resin to form the shield 137. The ultraviolet blocking or absorbing chemical can be added either by pre-compounding or tumble blending before molding the resin. As a further alternative, a transparent protective film or chemical having ultraviolet blocking or absorbing properties can be added to a product packaging for device 10 to further prevent degradation of the contents of the syringe 50.

The housing 12 can also include a portion 139 of increased strength proximate the window 130. For example, and as depicted in FIG. 7, the portion 139 can be provided with a non-cylindrical configuration, such as a bulbous or barrel-shaped portion, for additional strength. The portion 139 of the housing 12 can be wider near the window 130 relative to the remainder of the housing 12. The portion 139 can increase the strength and thus resist deformation of the housing 12, which can otherwise be weakened by the loss of material in the housing 12 to form the window 130. Additionally, the contoured housing can improve ergonomics and aesthetics of the automatic injection device 10.

Although reference is made to certain features on a front of the device 10 or components, such as window 130, first and second openings 505, 501, shroud notch 115, cap notch 250, such features can include, for example, a corresponding, diametrically opposed feature on a rear of the device, or other suitable location on the device 10.

The automatic injection device of the disclosed subject matter can be used for injection or delivery of any of a variety of suitable liquid substances of corresponding volume or dose.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A syringe carrier for use within an automatic injection device comprising:
    a substantially tubular body having a first end, a middle portion, and a second end, configured to contain a portion of a syringe and displace the syringe within a housing of the automatic injection device from a first position to a second position;
    a first pair of legs defining at least a portion of a front opening in the substantially tubular body proximal to the first end;
    a second pair of legs defining at least a portion of a rear opening in the substantially tubular body proximal to the first end; and
    a syringe carrier coupler having a first beam and a second beam extending from the middle portion partially beyond the first pair of legs at the first end of the substantially tubular body.

2. The syringe carrier of claim 1, wherein the first pair of legs and the second pair of legs are distributed circumferentially about the substantially tubular body of the syringe carrier.

3. The syringe carrier of claim 1, wherein the second end includes a second opening configured to align with a window in the middle portion when the syringe carrier is in the second position.

4. The syringe carrier of claim 1, wherein the middle portion of the syringe carrier is sized to resist deformation of the syringe carrier.

5. The syringe carrier of claim 1, wherein the first pair of legs extends from the middle portion of the syringe carrier and each leg is tapered with a greater cross-dimension proximate the middle portion of the syringe carrier.

6. The syringe carrier of claim 1, wherein a portion of the first pair of legs is configured to engage at least one interior stop of the housing to prevent movement of the syringe carrier toward the second position.

7. The syringe carrier of claim 6, wherein each leg of the first pair of legs includes an anchor portion to engage the at least one interior stop to prevent movement of the syringe carrier toward the second position.

8. The syringe carrier of claim 7, wherein the anchor portion of each leg projects radially outwardly.

9. The syringe carrier of claim 7, wherein the anchor portion includes at least one projection sized to prevent movement of the syringe carrier away from the second position.

10. The syringe carrier of claim 7, wherein the anchor portion includes a first projection sized to prevent movement of the first projection past the at least one interior stop of the housing to prevent movement of the syringe carrier away from the second position, and a second projection sized to prevent movement of the syringe carrier toward the second position until the syringe carrier is urged in the direction of the second position to move the second projection past the at least one interior stop.

11. The syringe carrier of claim 10, wherein the first projection extends radially outward beyond the second projection.

12. The syringe carrier of claim 10, wherein the second projection comprises an arcuate surface portion and the interior stop comprises a chamfered edge portion configured to abut the arcuate surface portion when the syringe carrier is urged toward the second position.

13. The syringe carrier of claim 1, wherein the first position is a pre-injection position and the second position is a post-injection position.

14. A syringe carrier for use within an automatic injection device comprising:
a substantially tubular body having a first end, a middle portion, and a second end, configured to contain a portion of a syringe and displace the syringe within a housing of the automatic injection device from a first position to a second position;
a first pair of legs defining at least a portion of a first opening in the substantially tubular body proximal to the first end;
a second opening spaced from the first end and aligned with the first opening along a length of the syringe carrier; and
a syringe carrier coupler having a first beam and a second beam extending from the middle portion partially beyond the first pair of legs at the first end of the substantially tubular body.

15. The syringe carrier of claim 14, further comprising a second pair of legs defining at least a portion of a second opening diametrically opposite the first opening.

16. The syringe carrier of claim 14, wherein the second end includes a second opening configured to align with a window in the middle portion when the syringe carrier is in the second position.

17. The syringe carrier of claim 14, wherein the middle portion of the syringe carrier is sized to resist deformation of the syringe carrier.

18. The syringe carrier of claim 14, wherein the first pair of legs extends from the middle portion of the syringe carrier and each leg is tapered with a greater cross-dimension proximate the middle portion of the syringe carrier.

19. The syringe carrier of claim 14, wherein a portion of the first pair of legs is configured to engage at least one interior stop of the housing to prevent movement of the syringe carrier toward the second position.

20. The syringe carrier of claim 19, wherein each leg of the first pair of legs includes an anchor portion to engage the at least one interior stop to prevent movement of the syringe carrier toward the second position.

* * * * *